United States Patent [19]
Cerami et al.

[11] Patent Number: 5,863,535
[45] Date of Patent: Jan. 26, 1999

[54] MACROPHAGE-DERIVED INFLAMMATORY MEDIATOR (MIP-1α AND MIP-1β)

[75] Inventors: Anthony Cerami, Shelter Island, N.Y.; Bruce Beutler, Dallas, Tex.; Stephen D. Wolpe, New York, N.Y.

[73] Assignee: The Rockefeller University, New York, N.Y.

[21] Appl. No.: 476,378

[22] Filed: Jun. 7, 1995

Related U.S. Application Data

[62] Division of Ser. No. 207,888, Mar. 7, 1994, Pat. No. 5,616,688, which is a continuation of Ser. No. 24,867, Mar. 1, 1993, abandoned, which is a continuation of Ser. No. 902,532, Jun. 22, 1992, abandoned, which is a continuation of Ser. No. 238,937, Sep. 2, 1988, abandoned, which is a continuation of Ser. No. 104,827, Oct. 2, 1987, abandoned, which is a continuation-in-part of Ser. No. 766,852, Aug. 16, 1985, which is a continuation-in-part of Ser. No. 414,098, Sep. 7, 1982, Pat. No. 4,603,106, which is a continuation-in-part of Ser. No. 351,290, Feb. 22, 1982, abandoned, which is a continuation-in-part of Ser. No. 299,932, Sep. 8, 1981, abandoned.

[51] Int. Cl.$^6$ .................. A61K 45/05; A61K 39/395; C07K 1/00; C07K 14/00
[52] U.S. Cl. ................. 424/130.1; 424/85.1; 530/350; 530/351
[58] Field of Search ............................ 530/351, 350; 424/85.1

[56] References Cited

U.S. PATENT DOCUMENTS

| 4,603,106 | 7/1986 | Cerami et al. . |
| 5,145,676 | 9/1992 | Fahey, III et al. . |

FOREIGN PATENT DOCUMENTS

WO 83/00930  3/1983  WIPO .

OTHER PUBLICATIONS

Sherry et al. (1992) Cytokines 4: 117–30.
Sherry et al. (1991) Curr. Opin. Immunol. 3: 56–60.
Dinarello et al. (1977) Proc. Natl. Acad. Sci. USA 74: 4624–7.
Voller et al. (1976) Bull. World Health Organ. 53:55–65.
Brown et al. (1972) Bioch. Biophys. Res. Commun: 375–82.
Brown et al. (1989) J. Immunol. 142: 679–87.
Sporn et al. (1989) J. Immunol. 144: 4434–4441.
Wolpe et al. (1989) FASEB J. 3: 2565–73.
Yoshimura et al. (1989) FEBS Letts. 224:487–93.
Zipfel et al. (1989) J. Immunol. 142: 1582–90.
Davatelis et al. (1988) J. Exp. Med. 167: 1939–44.
Lipes et al. (1988) Proc. Natl. Acad. Sci. USA 85: 9704–8.
Matsushima et al. (1988) J. Exp. Med. 167: 1883–93.
Sherry et al. (1988) J. Exp. Med. 168: 2251–9.
Wolpe et al. (1988) J. Exp. Med. 167: 570–81.
Sassa et al. (1987) Blood Cells 13: 161–9.
Wolpe et al. (1987) in The inhibitors of hamatopoiesis. Najman et al. eds. pp. 197–200.
Yoshimura et al. (1987) J. Immunol. 139: 788–93.
Yoshimura et al. (1987) Proc. Natl. Acad. Sci. USA 84: 9233–7.
Caput et al. (1986) Proc. Natl. Acad. Sci. USA 83: 1670–4.
Reeves et al. (1986) Proc. Natl. Acad. Sci. USA 83: 3228–32.
Kownatzki et al. (1986) Clin. Exp. Immunol. 64: 214–22.
Obaru et al. (1986) J. Biochem. 99: 885–94.
Beutler et al. (1985) Nature 316: 552–4.
Beutler et al. (1985) Science 229: 869–71.
Mahoney et al. (1985) J. Immunol. 134: 1673–1675.
Torti et al. (1985) Science 229: 867–9.
W.E. Paul, ed. (1984) Fundamental Immunology. p. 706.
Hotez et al. (1984) Parasite Immunol. 6:203.
Lomdedico et al. (1984) Nature 312: 458–62.
Kawakami et al. (1982) Proc. Natl. Acad. sci. USA: 79: 912–16.
Deuel et al. (1981) Proc. Natl. Acad. Sci. 78: 4584–7.
Kawakami et al. (1981) J. Exp. Med. 154: 631–9.
Merrill et al. (1980) J. Clin. Invest. 65: 268–76.
Kampschmidt et al. (1980) J. Lab. Clin. Med. 95: 616–23.
Tono–Oka et al. (1980) Immunol. 39: 607–13.
Sipe et al. (1979) J. Exp. Med. 150: 597–606.

*Primary Examiner*—Lynette F. Smith
*Attorney, Agent, or Firm*—Klauber & Jackson

[57] ABSTRACT

An inflammatory cytokine is disclosed which has been isolated from cells that have been incubated with a stimulator material. The inflammatory cytokine comprises a protein that is capable of binding to heparin, inducing localized inflammation characterized by polymorphonuclear cell infiltration when administered subcutaneously and inducing in vitro polymorphonuclear cell chemokinesis, while lacking the ability to suppress the activity of the anabolic enzyme lipoprotein lipase, cause the cytotoxicity of cachectin/TNF-sensitive cells, stimulate the blastogenesis of endotoxin-resistant C3H/HeJ thymocytes, or induce the production of cachectin/TNF by primary thioglycollate-elicited mouse macrophage cells. A particular inflammatory cytokine MIP-1 has been isolated and has been found to comprise a peptide doublet of similar molecular weights of about 8,000 daltons, and to show a pI of about 4.6. The doublet has been resolved into its component peptides, MIP-1α and MIP-1β for which distinct cDNA's have been cloned and sequenced. Diagnostic and therapeutic utilities are proposed, and testing procedures, materials in kit form and pharmaceutical compositions are likewise set forth.

16 Claims, 15 Drawing Sheets

```
 (1)                            (10)
Ala-Pro-Tyr-Gly-Ala-Asp-Thr-Pro-Thr-Ala- X - X -Phe-Ser-Tyr-Ser-Arg-Lys-Ile-
       (Met)             (Pro)                                       (Thr)
(20)                           (30)
 Pro-Arg-Gln-Phe-Ile-Val-Asp-Tyr-Phe-Glu-Thr-Ser-
```

FIG.3

```
ALA PRO TYR GLY ALA ASP THR PRO THR ALA CYS CYS PHE SER
TYR SER ARG LYS ILE PRO ARG GLN PHE ILE VAL ASP TYR PHE
GLU THR SER SER LEU CYS SER GLN PRO GLY VAL ILE PHE LEU
THR LYS ARG ASN ARG GLN ILE CYS ALA ASP SER LYS GLU THR
TRP VAL GLN GLU TYR ILE THR ASP LEU GLU LEU ASN ALA
```

FIG.7

```
          #22                              #30
          GLNPHEILEVALASPTYRPHEGLUTHR              Protein A  T           T T  T    A
          CA+TT+ATXGTXGA+TA+TT+GA+ACX              cDNA
             G  C           C C  C    G T  A           A A  A    T
          GT+AA+TAXCAXCT+AT+AA+CT+TGX              Coding
             C  G           G G  G    C T  A  A  A          A
       5'-GT+TC+AA+TA+TCXACXAT+AATTG-3'            Probe 1
             C  G  G  G          G T  A  A  A          A
       5'-GT+TC+TT+TA+TCXACXAT+AACTG-3'            Probe 2
             C  G**G  G          G  *
```

FIG.8

```
ALA PRO TYR GLY ALA ASP THR PRO THR ALA CYS CYS PHE SER TYR SER
ARG LYS ILE PRO ARG GLN PHE ILE VAL ASP TYR PHE GLU THR SER SER
LEU CYS SER GLN PRO GLY VAL ILE PHE LEU THR LYS ARG ASN ARG GLN
ILE CYS ALA ASP SER LYS GLU THR TRP VAL GLN GLU TYR ILE THR ASP
LEU GLU LEU ASN ALA
```

FIG.9

A ala-pro-tyr-gly-ala-asp-thr-pro-thr-ala- X - X -phe-ser-tyr-ser-arg-lys-ilepro-arg-gln-phe-ile-val-asp-tyr-phe-glu-thr-ser-

B ala-<u>pro-met-gly-ser-asp-pro-pro</u>-thr-ser- X - X -phe- X -tyr-

C
     (met)         (pro)                            (thr)
ala-pro-tyr-gly-ala-asp-thr-pro-thr-ala- X - X -phe-ser-tyr-ser-arg-lys-ilepro-arg-gln-phe-ile-val-asp-tyr-phe-glu-thr-ser-

FIG.13

ALA PRO MET GLY SER ASP PRO PRO THR SER CYS CYS PHE SER TYR THR
SER ARG GLN LEU HIS ARG SER PHE VAL MET ASP TYR TYR GLU THR SER
SER LEU CYS SER LYS PRO ALA VAL VAL PHE LEU THR LYS ARG GLY ARG
GLN ILE CYS ALA ASN PRO SER GLU PRO TRP VAL THR GLU TYR MET SER
ASP LEU GLU LEU ASN

FIG.14

MACROPHAGE-DERIVED INFLAMMATORY MEDIATOR (MIP-1α AND MIP-1β)

RELATED APPLICATIONS

The present application, is a Division of application Ser. No. 08/207,888 filed Mar. 7, 1994, now U.S. Pat. No. 5,616,688, which is a continuation of Ser. No. 08/024,867, filed Mar. 1, 1993, abandoned, which is a continuation of Ser. No. 07/902,532, filed Jun. 22, 1992, abandoned which is a continuation of Ser. No. 07/238,937, filed Sep. 2, 1988, abandoned, which is a continuation of Ser. No. 07/104,827, filed Oct. 2, 1987, now abandoned, which is a continuation in part of 06/766,852, filed Aug. 16, 1985, which is a continuation-in-part of Ser. No. 06/414,098, filed Sep. 7, 1982, now U.S. Pat. No. 4,603,106, which is a continuation-in-part of Ser. No. 06/351,290, filed Feb. 22, 1982, now abandoned, which is a continuation-in-part of Ser. No. 06/299,932, filed Sep. 8, 1981, which is now abandoned.

RELATED PUBLICATIONS

The Applicants are authors or co-authors of several articles directed to the subject matter of the present invention. These articles are in supplementation to those articles listed in U.S. Pat. No. 4,603,106, which earlier articles are incorporated herein by reference. (1) [Applicants Cerami and Beutler are co-authors with J. Mahoney, N. Le Trang and P. Pekala] "Purification of Cachectin, a Lipoprotein Lipase-Suppressing Hormone Secreted By Endotoxin-Induced RAW 264.7 Cells", J. EXP. MED. 161 at 984–995 (May, 1985); (2) [Applicants co-authored with J. R. Mahoney, N. Le Trang, W. Vine, and Y. Ikeda] "Lipopolysaccharide-Treated RAW 264.7 Cells Produce a Mediator Which Inhibits Lipoprotein Lipase in 3T3-L1 Cells", J. IMMUNOL. 134 (3) at 1673–1675 (March, 1985); (3) [Applicant Cerami a co-author with P. J. Hotez, N. Le Trang, and A. H. Fairlamb] "Lipoprotein Lipase Suppression in 3T3-L1 Cells by a Haematoprotozoan-Induced Mediator From Peritoneal Exudate Cells." PARASITE IMMUNOL. (Oxf.) 6:203 (1984); (4) [Applicants Cerami and Beutler co-authored with D. Greenwald, J. D. Hulmes, M. Chang Y.-C. E. Pan, J. Mathison and R. Ulevitch] "Identity of Tumor Necrosis Factor and Macrophage-Secreted Factor Cachectin", NATURE 316:552–554, (1985); (5) [Applicants Cerami and Beutler co-authored with F. M. Torti, B. Dieckmann and G. M. Ringold] "A Macrophage Factor Inhibits Adipocyte Gene Expression: An In Vitro Model of Cachexia" SCIENCE 229:867–869, (1985); (6) [Applicants Cerami and Beutler co-authored with I. W. Milsark] "Passive Immunization Against Cachectin/Tumor Necrosis Factor (TNF) Protects Mice From the Lethal Effect of Endotoxin", SCIENCE 229:869–871, (1985); and (7) [Applicants Cerami and Beutler co-authored with S. D. Wolpe, G. Davatelis, B. Sherry, D. G. Hesse, H. T. Nguyen, L. I. Moldawer, C. F. Nathan and S. F. Lowry] "Macrophages Secrete A Novel Heparin-Binding Protein With Inflammatory And Neutrophil Chemokinetic Properties", J. EXP. MED. 16F: 570–581 (1988). All of the above listed articles are incorporated herein by reference.

The research leading to the present invention was funded in part by grants from the National Institute of Health and the Rockefeller Foundation.

BACKGROUND OF THE INVENTION

The present invention is generally directed to materials and associated methods for the analysis and treatment of the effects and corresponding operation of invasive stimuli such as infection upon animal hosts, and in particular, is concerned with the identification of materials which may participate in the host response to such invasive stimuli.

Several common physiological and biochemical derangements have been observed in various mammalian hosts responding to a variety of invasive stimuli such as bacterial, viral or protozoal infection; tumors; or endotoxemia; as well as in idiopathic states. For example, these responses include fever, leukocytosis, hyperlipidemia, reduced food intake (anorexia), reduced activity, wasting (cachexia), and other modifications in muscle, white blood cell and liver metabolism. In particular, recent studies aimed at elucidating the biochemical mechanisms of cachexia in rabbits infected with *Trypanosoma brucei* noted that animals with a minimal parasite burden became moribund and exhibited an extreme hypertriglyceridemia, with a marked elevation of plasma very low density lipoprotein (VLDL). See C. A. Rouser and A. Cerami, MOL. BIOCHEM. PARASITOL. 1:31–38 (1980). The hypertriglyceridemic state was remarkable in view of the severe wasting diathesis that accompanied this experimental infection. The elevation of plasma VLDL was shown to result from a clearing defect, caused by a loss of peripheral tissue lipoprotein lipase (LPL) activity.

Reduced LPL activity has been observed by others, and it has been noted that this condition has existed when the human body was in shock. See E. B. Man, et al., "The Lipids of Serum and Liver in Patients with Hepatic Diseases", CLIN. INVEST. 24 at 623, et seq. (1945); See also John I. Gallin, et al., "Serum Lipids in Infection", N. ENGL. J. MED. 281 at 1081–1086 (Nov. 13, 1969); D. Farstchi, et al., "Effects of Three Bacterial Infections on Serum Lipids of Rabbits", J. BACTERIOL. 95 at 1615, et seq. (1968); S. E. Grossberg, et al., "Hyperlipaemia Following Viral Infection in the Chicken Embryo: A New Syndrome", NATURE (London) 208 at 954, et seq. (1965); Robert L. Hirsch, et al., "Hyperlipidemia, Fatty Liver and Bromsulfophthalein Retention in Rabbits Injected Intravenously with Bacterial Endotoxin", J. LIPID. RES. 5 at 563–568 (1964); and Osamu Sakaguchi, et al., "Alternations of Lipid Metabolism in Mice Injected With Endotoxins", MICROBIOL. IMMUNOL. 23 (2) at 71–85 (1979); R. F. Kampschmidt, "The Activity of Partially Purified Leukocytic Endogenous Mediator in Endotoxin Resistant C3H/HeJ Mice", J. LAB. CLIN. MED. 95 at 616, et seq. (1980); and Ralph F. Kampschmidt, "Leukocytic Endogenous Mediator", J. RET. SOC. 23 (4) at 287–297 (1978).

Additionally, publications are known by the Applicants that discuss the identification and existence of "mediators" that appear to be involved in the host response to infection; and in particular, the following articles, the texts of which are incorporated herein by reference, are listed: Sipe, J. D., et al., J. EXP. MED., 150:597–606 (1979); and Barney, C. C., et al., LIPTON, J. M. (Ed.), FEVER: INTERNATIONAL SYMPOSIUM, Dallas, Tex., Apr. 11–12, 1979 XII+263P. Raven Press: New York, Illus. ISBN 0-89004-451-1 (08877), 0 (0), pp.111–122 (1980); and Dinarello, C. A., "Human Leukocytic Pyrogen: Purification and Development of a Radioimmunoassay", PROC. NATL. ACAD. SCI. U.S.A., 74(10) at 4624–4627 (October, 1977). All of the factors identified and investigated by each of the authors in the above noted articles and the articles authored or co-authored by Kampschmidt have been determined to comprise a single grouping of factors which has been identified as interleukin-1 (IL-1). This determination has been documented in an article by Charles A. Dinarello, published in REVIEWS OF INFECTIOUS DISEASES, at Volume 6, No. 1 (January–February, 1984), the text of which is also incorporated herein by reference.

A similar deficiency of LPL activity was noted by Applicants in C3H/HeN mice after administration of *Escherichia coli* lipopolysaccharide (LPS). In contrast, the loss of LPL activity was not demonstrable in C3H/HeJ mice, which are genetically resistant to LPS. This resistance to endotoxin-induced LPL deficiency could be circumvented by the administration of serum obtained from endotoxin-sensitive animals that had been injected with LPS two hours previously. Similarly, resistance could be overcome by injecting conditioned medium from endotoxin-stimulated thioglycollate-elicited peritoneal macrophages obtained from sensitive mice. These findings were set forth in full detail in application Ser. No. 414,098, now U.S. Pat. No. 4,603,106, the disclosure of which is incorporated herein by reference.

The above work was prompted by the Applicants' belief that a "mediator" or "mediators" existed and were suspected to have a significant effect upon general metabolic activity of energy storage cells in the animal host. It was suspected that such "mediators" exerted a depressive effect upon the activity of certain anabolic enzymes, whose reduced activity was observed, for instance, where the host enters the condition known as shock, as in response to invasion. Resultingly, the relationship of the mediator produced by endotoxin-stimulated peritoneal mouse exudate cells, upon endotoxin-sensitive and endotoxin-insensitive mice alike, and the development through such investigation of a reagent for the measurement of anabolic enzyme activity was set forth in first filed abandoned application Ser. No. 299,932, incorporated herein by reference.

Further investigation of this system was made in conjunction with the 3T3-L1 "preadipocyte" model system, and the corresponding development of methods and associated materials for the development of antibodies to the "mediator" and other diagnostic procedures was then set forth in application Ser. No. 351,290, also incorporated herein by reference and now abandoned. Thereafter, in subsequent application Ser. No. 414,098, now U.S. Pat. No. 4,603,106, the Applicants established that the mediator substance that they had derived from the endotoxin stimulation of macrophage cells exhibited the activities of suppressing the anabolic enzymes lipoprotein lipase, acetyl Coenzyme A Carboxylase and fatty acid synthetase, and further, inhibited the growth and differentiation of erythroid-committed cells.

Additional work set forth in articles (1) and (4) by Beutler et al., and application Ser. No. 766,852, the disclosure of which is incorporated herein by reference, has resulted in the discovery that the earlier identified mediator substance contained a further protein component which possesses a number of activities, which distinguished it from both the mediator substance and the other factors identified in the art and known as Interleukin 1 and Interleukin 2. Further work set forth in article (f) by Beutler et al. and parent application Ser. No. 104,827, the disclosure of which is incorporated herein by reference, established the presence of an additional factor (MIP-1) in the mediator substance which demonstrates a distinguishable profile of activities.

Since that time, MIP-1 has been resolved into component peptides and the N-terminal sequences of two such peptides, now referred to as MIP-1α and MIP-1β, have been compared. Accordingly, the present application is directed to the newly discovered peptide isolates and the activities of MIP-1, and the applications both diagnostic and therapeutic to which these isolates may be put.

SUMMARY OF THE INVENTION

In accordance with the first aspect of the present invention, the inflammatory cytokine that is the newly discovered isolate of the mediator substance is disclosed, and comprises a protein that has been purified and is anionic under physiological conditions. The inflammatory cytokine of the present invention exhibits the ability to bind to heparin, even at high salt concentrations, to induce localized inflammation characterized by polymorphonuclear cell infiltration when administered subcutaneously and to induce in vitro polymorphonuclear cell chemokinesis. The present inflammatory cytokine however, lacks certain activities common to other factors that have been isolated from the mediator substance disclosed in U.S. Pat. No. 4,603,106.

In particular, the present inflammatory cytokine lacks the ability to suppress the activity of the anabolic enzyme lipoprotein lipase (LPL), and is unable to cause the cytotoxicity of cachectin/TNF-sensitive L929 cells, to stimulate the blastogenesis of endotoxin-resistant C3H/HeJ thymocytes, or to induce the production of cachectin/TNF by primary thioglycollate-elicited mouse macrophage cells. These latter characteristics all absent from the present inflammatory cytokine are exhibited by the known factors cachectin/TNF and interleukin-1 (IL-1), and thereby distinguish the present inflammatory cytokine therefrom.

Of the affirmative activities exhibited, the ability to bind to heparin and to induce localized inflammation characterized by polymorphonuclear (PMN) cell infiltration appear most significant. Accordingly, while the exact role that the present isolate plays in the cascade of reactions to host invasion is as yet ill defined, its participation in the elicitation of certain of the activities and conditions associated with mobilization against host invasion is clear. Accordingly, the inflammatory cytokine possesses the potential for use as a diagnostic tool to identify and perhaps differentiate between various stimuli whether invasive or idiopathic, by the activation of the present inflammatory cytokine that such stimuli may promote.

The present inflammatory cytokine was initially partially identified and characterized and found to contain certain polypeptide segments defining an apparent molecular weight of approximately 8,000 daltons as determined on polyacrylamide gel electrophoresis in the presence of sodium dodecyl sulphate (SDS-PAGE) with the tendency to form aggregates of high molecular weight greater than about $10^6$ daltons in low salt buffers. In particular, the present inflammatory cytokine has been noted to form aggregates greater than $2 \times 10^6$ daltons as assessed by gel filtration. Partial N-terminal amino acid sequence data as depicted in FIG. 2 herein, reveals no significant homology with any previously described proteins. By known cDNA cloning techniques based upon the partial peptide sequences determined, full translated peptide sequences were achieved, which have been found to possess molecular weights of approximately 8 kilodaltons. MIP-1 has been shown to have a pI of approximately 4.6 by chromatofocusing.

Further properties of the present inflammatory cytokine include its ability to induce fever in rabbits, and to induce superoxide formation or a respiratory burst in human neutrophils in vitro. These properties are illustrated in the data presented herein.

The present invention is also directed to the resolution of purified native MIP-1 which migrates as a doublet on SDS-PAGE with nearly identical apparent component molecular weights of about 8000 daltons. Chromatography on hydroxylapatite in the presence of SDS successfully separated the two components. Partial N-terminal sequence analysis of each component revealed that the two proteins are very similar in their N-terminal sequence but differ in the presence and positions of certain amino acids. In particular, the protein corresponding to the lower molecular weight band on SDS-PAGE (now termed "MIP-1α") had a partial N-terminal amino acid sequence identical to the major sequence observed and shown in FIG. 3 herein, whereas the higher molecular weight band (termed "MIP-1β") yielded an N-terminal sequence identical to the sequence obtained after substituting the minor amino acids at their respective positions. cDNA'S for both MIP-1α and MIP-1β have been cloned, allowing for the determination of the complete amino acid sequence of each of the peptide components, which sequences are depicted in FIGS. 10 and 15, respectively.

The cDNA for MIP-1α predicts a mature protein of 69 amino acids in length with a predicted molecular mass of 7,889. There are no apparent sites for N-glycosylation. The cDNA for MIP-1β predicts a mature protein also of 69 amino acids in length with a predicted molecular mass of 7,832 daltons. There is one potential N-glycosylation site (Asn-Pro-Ser) at positions 53 to 55.

As mentioned earlier, the present inflammatory cytokine may be prepared by the stimulation of animal cells with a material such as might accompany an invasive stimulus. In particular, a sample of macrophage cells which may be derived from a variety of sources may be incubated with a stimulator material such as endotoxin or trypanosomes, to produce the mediator substance disclosed in U.S. Pat. No. 4,613,106. Such incubation may take place for a period of time of up to twenty hours, and exact time limits will vary with the particular cells selected for incubation.

Following such incubation, the medium may be appropriately treated as by centrifuging, to remove a supernatant containing the crude mediator substance. The mediator substance may then be further treated as by filtration or precipitation. Thereafter, the crude mediator substance may be subjected to a series of known isolation techniques, whereupon the inflammatory cytokine may be recovered. The present invention naturally contemplates alternate means for preparation of the inflammatory cytokine, including where applicable known genetic replicative techniques, and the invention is accordingly intended to cover such synthetic preparations within its scope.

As noted above, the present invention also includes the identification of the purified peptide components of the present cytokine that exhibit in combination the above noted activities and characteristics, that display the amino acid sequences set forth below and in FIGS. 10 and 15, as determined in mice.

MIP-1α

ALA PRO TYR GLY ALA ASP THR PRO THR ALA CYS CYS PHE SER TYR SER ARG LYS ILE PRO ARG GLN PHE ILE VAL ASP TYR PHE GLU THR SER SER LEU CYS SER GLN PRO GLY VAL ILE PHE LEU THR LYS ARG ASN ARG GLN ILE CYS ALA ASP SER LYS GLU THR TRP VAL GLN GLU TYR ILE THR ASP LEU GLU LEU ASN ALA

MIP-1β

ALA PRO MET GLY SER ASP PRO PRO THR SER CYS CYS PHE SER TYR THR SER ARG GLN LEU HIS ARG SER PHE VAL MET ASP TYR TYR GLU THR SER SER LEU CYS SER LYS PRO ALA VAL VAL PHE LEU THR LYS ARG GLY ARG GLN ILE CYS ALA ASN PRO SER GLU PRO TRP VAL THR GLU TYR MET SER ASP LEU GLU LEU ASN

As stated earlier, the foregoing sequence bears no striking similarity to any of the known mediator factors and accordingly establishes that the present inflammatory cytokine is distinguishable therefrom. The recent isolation of the above amino acid sequences and the development of the mRNA sequence have facilitated the reproduction of this cytokine by conventional recombinant genetic techniques.

The invention further includes methods for identifying idiopathic or invasive stimuli on the basis of their ability to induce the present inflammatory cytokine or the activities that it affects. In particular, such stimuli could be identified and detected by their ability to induce mediators which bind to heparin and induce localized inflammation with neutrophil infiltration and chemokinesis. In this method, macrophage cells derived for example, from the RAW 264.7 cell line could be inoculated with a number of known stimulator materials such as endotoxin, trypanosomes or the like, as a control, while parallel cellular samples could be inoculated with an extract of material from the presumed situs of the infective stimulus. All samples could thereafter be incubated in accordance with the methods described above, and thereafter subjected to the sequence of separation techniques also defined, whereupon testing of the resulting isolates derived from the control and unknown samples could be compared to determine whether the inflammatory cytokine, if any, developed is identical or even similar.

Alternatively, altered mRNA levels of the inflammatory cytokine could be detected by techniques used in the art that make use of cDNA sequences disclosed herein.

In similar fashion, an assay system for screening of potential drugs effective to either mimic or counteract the inflammatory cytokine may be prepared. In one instance, the test drug could be administered to a stimulated macrophage sample to determine its effect upon the production of the inflammatory cytokine. In an alternate procedure, the inflammatory cytokine may be introduced into a cellular test system in which the cytokine is known to be active, and the prospective drug may also be introduced to the same cell culture and the culture may thereafter be examined to observe any changes in the activity of the inflammatory cytokine in comparison with the addition of the prospective drug alone, or the effect of added quantities of the known inflammatory cytokine.

The present invention also relates to a method for determining the presence of stimulated, spontaneous, or idiopathic pathological states in mammals, by measuring the activity and presence of the inflammatory cytokine of the present invention. More particularly, the activity of the inflammatory cytokine may be followed directly by the assay techniques discussed later on, through the use of an appropriately labeled quantity of the cytokine. Alternately, the cytokine can be used to raise binding partners or antibodies that could in turn, be labeled and introduced into a medium such as serum, to test for the presence of inflammatory cytokine therein, and to thereby assess the state of the host from which the medium was drawn.

Thus, both the inflammatory cytokine and any antibodies that may be raised thereto, are capable of use in connection with various diagnostic techniques, including immunoassays, such as a radioimmunoassay, using for example, an antibody to the inflammatory cytokine that has been labeled by either radioactive addition, reduction with sodium borohydride, or radioiodination.

In an exemplary immunoassay, a control quantity of the inflammatory cytokine, its antibody, or the like may be prepared and labeled with an enzyme, a specific binding partner and/or a radioactive element, and may then be introduced into a blood sample of a mammal believed to be undergoing invasion. After the labeled material or its binding partner(s) has had an opportunity to react with sites within the sample, the resulting mass may be examined by known techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized calorimetric, spectrophotometric, fluorospectrophotometric or gasometric techniques known in the art.

The present invention includes an assay system which may be prepared in the form of a test kit for the quantitative analysis of the extent of the presence of the inflammatory cytokine. The system or test kit may comprise a labeled component prepared by one of the radioactive and/or enzymatic techniques discussed herein, coupling a label to the inflammatory cytokine; and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the inflammatory cytokine, antibodies to the inflammatory cytokine, or upon other agents or drugs determined to possess the same or an antagonistic activity. A first therapeutic method is associated with the prevention of the manifestations of the activities of the inflammatory cytokine in mammals, such as inflammation and fever, and comprises administering either an antibody to the cytokine, an agent capable of modulating the production and/or activity of the cytokine, or an agent not an antibody to the cytokine that is capable of acting as an antagonist to the cytokine, either individually or in mixture with each other in an amount effective to prevent the development of those conditions in the host.

More specifically, the therapeutic method generally referred to herein could include the method for the treatment of inflammation and fever by the administration of pharmaceutical compositions that may comprise effective quantities of antibodies to the inflammatory cytokine, or other equally effective drugs developed, for instance, by a drug screening assay prepared and used in accordance with a further aspect of the present invention. A variant embodiment of this therapeutic method could include initially detecting the presence and activity of the inflammatory cytokine and thereafter admininstering the appropriate pharmaceutical composition.

A second therapeutic method seeks to take advantage of the inflammatory activity of the cytokine and in particular, its ability to cause the movement and mobilization of neutrophils in response to invasive stimuli such as infection. Accordingly, the inflammatory cytokine may be prepared in a suitable formulation for administration to the situs of infection which for example, may develop where tissue trauma has occurred. In such instance, the inflammatory cytokine prepared in a sterile solution and delivered to the trauma or wound as part of an irrigation fluid or by direct dosage such as, in a pharmaceutical composition, the latter course of administration contemplating topical and parenteral routes. Naturally, the inflammatory cytokine may be used to raise equally effective agents or drugs by known methods that may then be formulated into pharmaceutical compositions suitable for administration in the same manner and for the same purpose as for the inflammatory cytokine itself.

Accordingly, it is a principal object of the present invention to provide an inflammatory cytokine in purified form that exhibits certain characteristics and activities associated with the host response to invasive stimuli in mammals.

It is a further object of the present invention to provide a method for the preparation of the inflammatory cytokine.

It is a further object of the present invention to provide a method for detecting the presence of the inflammatory cytokine in mammals in which invasive, spontaneous, or idiopathic pathological states such as infection are suspected to be present.

It is a further object of the present invention to provide a method and associated assay system for screening substances such as drugs, agents and the like, potentially effective in either mimicking the activity or combating the adverse affects of the inflammatory cytokine in mammals.

It is a still further object of the present invention to provide a method for the treatment of mammals to control the amount or activity of the inflammatory cytokine, so as to alter the consequences of such presence or activity.

It is a still further object of the present invention to provide a method for the treatment of mammals to promote the amount or activity of the inflammatory cytokine, so as to treat or avert the adverse consequences of invasive, spontaneous or idiopathic pathological states.

It is a still further object of the present invention to provide pharmaceutical compositions for use in therapeutic methods which comprise or are based upon the inflammatory cytokines or their binding partner(s), or upon agents or drugs that control the production, or that mimic or antagonize the activities of the inflammatory cytokine.

Other objects and advantages will become apparent to those skilled in the art from a review of the ensuing description which proceeds with reference to the following illustrative drawings.

BRIEF DESCRIPTION OF THE DRAWINGS

FIG. 3 depicts a partial amino acid sequence of the first 31 positions of the inflammatory cytokine of the present invention. Residues in parentheses indicate positions at which "minor" residues were reproducibly obtained in different sequence runs on different batches of material.

FIG. 7 is a graphical depiction of the results of tests for the ability of the inflammatory cytokine to stimulate $H_2O_2$ release by human neutrophils (PMN'S). Human PMN'S incubated in serum-coated microtest plate wells were treated at time 0 with PMA (100 ng/ml) (○), recombinant cachectin/TNF (10 ng/ml) (Δ), MIP-1 (1000 ng/ml) (o) or an equivalent volume of buffer alone (control) (▲). $H_2O_2$ release was monitored over the next 4.5 hours (2 hours for cachectin/TNF). Values are means±SEM for triplicates in one of 4 similar experiments.

FIG. 8 is a depiction of the amino acid sequence of the inflammatory cytokine MIP-1 of the present invention as initially recovered from mice.

FIG. 9 depicts 512-fold degeneracy probe pools used in the cDNA cloning of MIP-1α. An asterisk below a base indicates a constant base change between the two-probe pools.

FIG. 13 is a graphical depiction of the fractionation of MIP-1 into component peptides by SDS-hydroxylapatite chromatography. MIP-1 (500 μg) was applied to SDS-hydroxylapatite and fractionated as described. 0.5 ml fractions were collected, analyzed by SDS-PAGE, and pooled as indicated by underline.

FIG. 14 depicts N-terminal amino acid sequences: (A) The N-terminal amino acid sequence of purified MIP-1α; (B) The N-terminal amino acid sequence of purified MIP-1β, the residues underlined (2–8) were those used to construct an oligonucleotide probe pool; (C) The original N-terminal amino acid consensus sequence reported for purified native MIP-1. Amino acid residues corresponding to the minor residues are given in parenthesis.

DETAILED DESCRIPTION

Figure 1B:
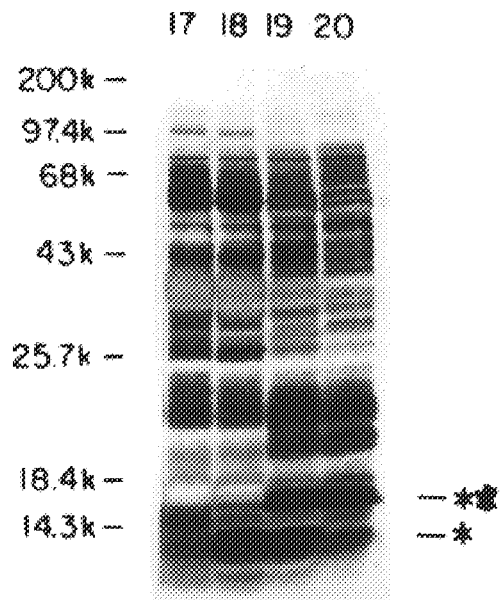
FIG. 1 is a combined graphical and electrophoretic gel depiction of the preparation and recovery of the inflammatory cytokine from a supernatant of RAW 264.7 cells. Fractionation of the concentrated, diafiltrated supernatant from RAW 264.7 was performed on MONO Q anion exchange column. Two liters of supernatant (mediator substance) were concentrated twenty times and diafiltrated against six liters of 20 mM Tris-HCl, pH 8.0. The concentrated supernatant was applied to MONO Q anion exchange column and eluted with a linear gradient of 0 to 1M NaCl in the same buffer. MIP-1 (*) eluted slightly before cachectin/TNF (**) at approximately 0.37M NaCl. The insert shows a 10–15% SDS-PAGE gel to which 50 μl from the indicated fractions have been applied.

In its primary aspect, the present invention concerns the isolation and identification of a particular factor hereinafter referred to as inflammatory cytokine or macrophage inflammatory protein, MIP-1, that has been found to be present in or secreted by macrophages or macrophage cell lines that are stimulated by materials referred to herein as stimulator materials, that characteristically accompany an invasive stimulus, such as bacteria, viruses, certain tumors, protozoa and other toxins such as endotoxin, or an idiopathic state. The present invention also pertains to the resolution of MIP-1 into its component peptides, MIP-1α and MIP-1β. As with the mediator substance disclosed in U.S. Pat. No. 4,603,106, the present inflammatory cytokine, which has been determined to be a component of the former mediator substance, appears to be capable of causing certain conditions such as inflammation to develop in the tissues of a mammal, which reflect the reaction of a mammal in a stimulated or spontaneous pathological state.

In particular, the inflammatory cytokine appears to be capable of inducing localized inflammation when administered subcutaneously which inflammation is characterized by polymorphonuclear cell infiltration. Also, the cytokine causes in vitro polymorphonuclear cell chemokinesis, which conditions are reflective of the influence of a cytokine involved in mobilization by the mammalian host against an invasive stimulus. While the full and exact role played by the present inflammatory cytokine is unclear, it is theorized that the cytokine in conjunction with other factors previously identified and those yet to be elucidated, functions as part of a communication system between the immune system of the host and other body tissues and organs.

The ability of the present inflammatory cytokine to bind to heparin gave rise to the consideration that the cytokine might correspond to certain heparin-binding growth factors such as FGF or PDGF. However, data indicating that the inflammatory cytokine is not mitogenic for smooth muscle cells suggests a distinction from these known growth factors. Accordingly, what is certain at this time, is that the cytokine of the present invention participates in the development of the inflammatory response that is known to to be a part of host responses such as to invasion.

As indicated earlier, the present inflammatory cytokine has been confirmed to comprise a protein that possesses an isoelectric point (pI) of approximately 4.6. The inflammatory cytokine can be isolated as a doublet with nearly identical subunit molecular weights of approximately 8,000 daltons and may form multimers of various molecular weights up to and exceeding $2 \times 10^6$ daltons as assessed by the results of the investigations that led to its isolation, which are set forth in the Example below. These investigations likewise identified the N-terminal peptide sequences, and the full sequence thereafter developed by known genetic replicative techniques confirm that the specific peptide sequences of the present inflammatory cytokine differ from that of other known mediator factors. Accordingly, both structural and functional distinctions between the present inflammatory cytokine and the known mediator factors of the prior art exists as is confirmed by the data set forth in the Example.

More particularly, the inflammatory cytokine of the present invention possesses certain other characteristics in conjunction with those outlined above, in that it is capable of binding to heparin at high salt concentrations, e.g. approximately 0.7M. A further characteristic of the present inflammatory cytokine is that it is anionic under physiological conditions. The cytokine is also distinctive in those activities that it lacks, such as the inability to suppress the anabolic enzyme lipoprotein lipase (LPL), to cause the cytotoxicity of cachectin/TNF-sensitive L929 cells, stimulate the blastogenesis of endotoxin-resistant C3H/HeJ thymocytes or to induce the production of cachectin/TNF by primary thioglycollate-elicited mouse macrophage cells. All of these latter activities are those shared by the other known macrophage-derived mediator factors whose general characteristics and activities have identified them as participants in the host response to invasion. This accordingly distinguishes the present inflammatory cytokine from those known factors and confirms in conjunction with the cDNA and protein sequencing data presented herein, that the present inflammatory cytokine is indeed distinct from the other macrophage-derived mediator factors.

The inflammatory cytokine in accordance with the present invention was isolated and analyzed in mice as set forth in the Example herein. Further work of cloning and sequencing the cDNA of the message for the distinct polypeptides of the inflammatory cytokine performed after the completion of the experiments set forth in the Example has resulted in the elucidation of the complete sequence of the peptides MIP-1α and MIP-1β, and their sequences are presented herein in FIGS. 10 and 15, respectively. It has therefore been determined that the purified inflammatory protein is defined by two sequences each of 69 amino acids.

A cDNA library was prepared from endotoxin-stimulated RAW 264.7 cells and was screened using two synthetic oligonucleotide pools based on the "major" partial N-terminal amino acid sequence of MIP-1. The cDNA so cloned is shown to correspond to the peptide chain now known as MIP-1α. The cDNA for MIP-1β was cloned using a similar strategy, although here the oligonucleotide pool used was derived from a portion of the molecule in which three of the seven amino acid residues are different from the corresponding residues in MIP-1α.

The cDNA for MIP-1α predicts a mature protein of 69 amino acids in length with a predicted molecular mass of 7,889. There are no apparent sites for N-glycosylation. The cDNA for MIP-1β predicts a mature protein also 69 amino acids in length with a predicted molecular mass of 7,832 daltons in which there is one potential N-glycosylation site (Asn-Pro-Ser) at position 53–55. As MIP-1β migrates on SDS-PAGE as a slightly larger molecule than MIP-1α, it is possible that it is glycosylated. It is known that proline at position X in the Asn-X-Ser,Thr signal for N-linked glycosylation results in impaired or absent glycosylation at that site. This may account for the relatively small difference in molecular mass between MIP-1α and MIP-1β should the latter be glycosylated.

Experiments are now under way to express the recombinant form of this disclosed protein. Human inflammatory cytokine MIP-1 is presumably similar to mouse MIP-1, since the mouse MIP-1 has an effect upon human neutrophils. As disclosed herein, this activity of the inflammatory cytokine may be harnessed by administering the inflammatory cytokine to the situs of tissue infection to promote the delivery of neutrophils to that location.

The genetic replication of the inflammatory cytokine involves many of the general principles of recombinant technology that are well known in the art, and accordingly a detailed presentation of such techniques is not deemed to be necessary and is not presented herein. The present invention, however, contemplates the preparation of the present inflammatory cytokine, and in particular the material having the amino acid sequences set forth in FIGS. 10 and 15, by known recombinant techniques. The preparation of the inflammatory cytokine was discussed in brief earlier herein, and is confirmed to be capable in one aspect of proceeding by the initiation of the incubation of any of a variety of cells with stimulator materials such as from invasive stimuli. In particular, the cell line RAW 264.7 may be utilized to initiate the production of the mediator substance from which the inflammatory cytokine may be isolated. The murine macrophage cell line RAW 264.7 has facilitated the isolation of the inflammatory cytokine in quantities large enough to permit analysis and purification. Naturally, other cell lines or other sources for the development of either the material from which the inflammatory cytokine is thereafter isolated (mediator substance), or the inflammatory cytokine or its constituent peptides, are contemplated herein and the present invention is accordingly not limited. Thus, alternate means such as by genetic replication are contemplated herein in accordance with the present invention.

As discussed earlier, the inflammatory cytokine, its constituent peptides, their binding partner(s) or other ligands or agents exhibiting either mimicry or antagonism to the cytokine or control over its production, may be prepared in pharmaceutical compositions, with a suitable carrier and at a strength effective for administration by various means to a patient having a tissue infection or other pathological derangement, for the treatment thereof. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, including delivery in an irrigation fluid used to wash body wound areas, catheterization and the like. Average quantities of the inflammatory cytokine and/or the above recited related agents may vary and in particular should be based upon the recommendations and prescription of a qualified physician or veterinarian.

As stated above and as indicated earlier, antibodies and drugs that modulate the production or activity of the inflammatory cytokine may possess certain therapeutic applications and may thus be utilized for the purpose of treating the effects attributable to the action of the inflammatory cytokine, such as inflammation and fever. In particular, the inflammatory cytokine may be used to produce antibodies to itself in a variety of mammals, by known techniques such as the hybridoma technique utilizing, for example, fused mouse spleen lymphocytes and myeloma cells. The resulting antibodies could then be prepared in a suitable pharmaceutical composition and administered to avert or treat the undesired condition. The exact quantities, intervals of administration and administrative techniques respecting such pharmaceutical compositions may vary in accordance with those known in the medical arts, and upon the specific instruction of a qualified physician or veterinarian.

The present invention also relates to a variety of diagnostic applications, including methods for determining the presence of invasive stimuli by reference to their ability to elicit the activities which are affected by the present inflammatory cytokine. As mentioned earlier, the inflammatory cytokine can be used to produce antibodies to itself by a variety of known techniques, and such antibodies could then be isolated and utilized as in tests for the presence of the inflammatory cytokine in suspect mammals.

Antibody(ies) to the peptides of the inflammatory cytokine can be produced and isolated by standard methods including the well known hybridoma techniques. For convenience, the antibody(ies) to the inflammatory cytokines will be referred to herein as $Ab_1$ and antibody(ies) raised in another species as $Ab_2$.

The presence of inflammatory cytokine activity in mammals can be ascertained by the usual immunological procedures applicable to such determinations. A number of useful procedures are known. Three such procedures which are especially useful utilize either the inflammatory cytokine labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Cyt" stands for the inflammatory cytokine:

A. $Cyt^* + Ab_1 = Cyt^*Ab_1$
B. $Cyt + Ab^* = CytAb_1^*$
C. $Cyt + Ab_1 + Ab_2^* = CytAb_1Ab_2^*$

The procedures and their application are all familiar to those skilled in the art and are presented herein as illustrative and not restrictive of procedures that may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the inflammatory cytokine forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because antibodies raised in one mammalian species have been used in another species as an antigen to raise antibodies such as $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-inflammatory cytokine antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The peptides of the inflammatory cytokine or their binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the inflammatory cytokine may be radiolabeled, after which binding studies would be carried out using for example, recently differentiated neutrophils. Solutions would then be prepared that contain various quantities of labeled and unlabeled inflammatory cytokine and unknown cell samples would then be inoculated and thereafter incubated. The resulting cell monolayers would then be washed, solubilized and then counted in a gamma counter for a length of time sufficient to yield a standard error of <5%. These data are then subjected to Scatchard analysis after which observations and conclusions regarding material activity can be drawn. While the foregoing protocol is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of inflammatory cytokine in a suspected mammal. For example, one class of such kits will contain at least a labeled component selected from the inflammatory cytokine or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the reaction of a mammalian host to invasive stimuli, comprising:

(a) a predetermined amount of at least one labeled immunochemically reactive component obtained by the direct or indirect attachment of the present inflammatory cytokine or a specific binding partner thereto, to a detectable label;

(b) other reagents; and (c) directions for use of said kit.

More specifically, the diagnostic test kit may comprise:

(a) a known amount of the inflammatory cytokine as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the inflammatory cytokine to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the inflammatory cytokine and a specific binding partner thereto.

In accordance with the above, an assay system for screening potential drugs effective to modulate the synthesis, release, or activity of the inflammatory cytokine may be prepared. In a first procedure, the test drug could be administered to a stimulated macrophage sample to determine its effect upon the production of the inflammatory cytokine. In an alternate procedure, the inflammatory cytokine may be introduced into a cellular test system such as neutrophils, and the prospective drug may also be introduced into the cell culture, and the culture thereafter examined to observe any changes in the activity of the inflammatory cytokine, either resulting from the addition of the prospective drug alone, or from the effect of added quantities of the known inflammatory cytokine.

Figure 10:
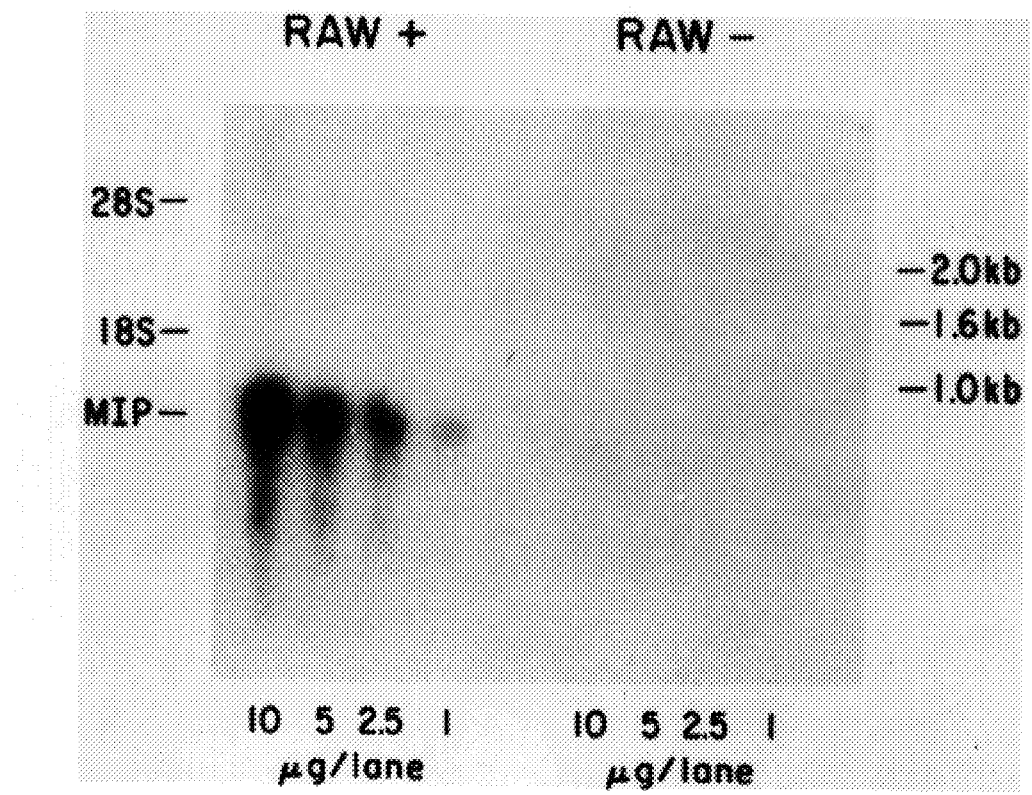
FIG. 10 depicts the complete nucleotide sequence of a cDNA clone for MIP-1α. The underlined sequence indicates the complementary sequence of the oligonucleotide used in primer extension experiments. The predicted translated molecular weight of the precursor peptide is 10,346. The mature peptide sequence, starting at position one, is 69 amino acids in length and has a predicted molecular weight of 7,889.
Figure 15:
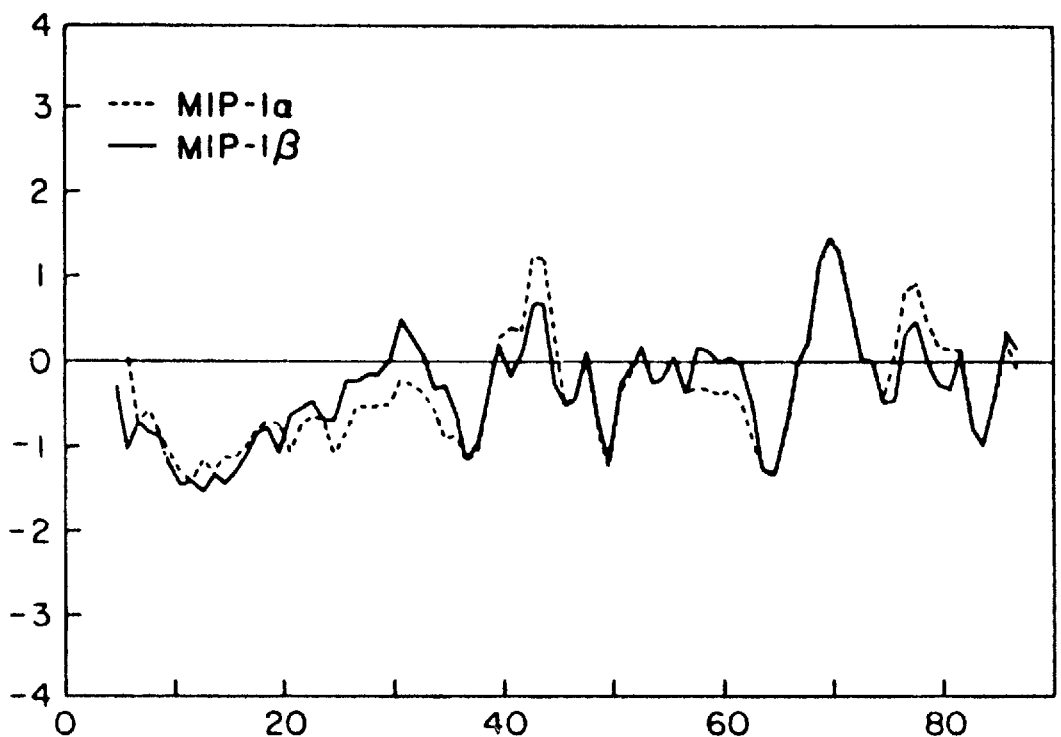
FIG. 15 depicts the complete nucleotide sequence of the cDNA clone for MIP-1β. The predicted translated molecular weight is 10,169 daltons. The mature protein sequence, starting at position one, is 69 amino acids in length and has a predicted molecular weight of 6993 daltons.

The primary amino acid sequences shown in FIGS. 10 and 15 are only illustrative of the proteins useful in the present invention and similar sequences may result in proteins which have substantially equivalent or altered activity as compared to that set forth in FIGS. 10 and 15. These modifications may be deliberate, for example, such as modifications obtained through site-directed mutagenesis, or may be accidental, such as those obtained through mutations in hosts which are MIP-1 producers. All of these modifications are included in the present invention, as long as the MIP-1-like activity, as defined above, is retained. Accordingly, the definition of MIP-1 and the term "inflammatory cytokine" as used herein specifically includes protein material with peptide components having an amino acid sequence substantially equivalent to that in FIGS. 10 and 15, either individually or in combination.

Similarly, the term "stimulus" and its plural are intended to apply to invasive events such infection, as well as conditions caused by wounding, and to idiopathic or spontaneous states that may for example originate from cellular or metabolic derangements or other causes.

As indicated earlier, the following example sets forth the details of the isolation and identification of the present inflammatory cytokine, and the observations noted as to its activity, defining both the distinctions and similarities in activity between the present inflammatory cytokine and those factors identified earlier both by applicants and by others in the field. Naturally, the specific materials and techniques set forth hereinafter are exemplary only and may vary, so that the following is presented as illustrative but not restrictive of the present invention.

EXAMPLE

The following experiments were conducted to identify and further characterize the inflammatory cytokine of the present invention. Initially, the mediator substance was cultured, the inflammatory cytokine was isolated and its structure then determined, after which a battery of tests were conducted in an effort to elucidate its activities, and where possible, to establish or refute identity with other known macrophage-derived factors.

MATERIALS AND METHODS

Materials—Purified, recombinant human cachectin/TNF was obtained from Chiron Corp., Emeryville, Calif. Purified, recombinant human IL-1α was the generous gift of Dr. P. Lomedico (Hoffmann LaRoche, Nutley, N.J.). All chemicals were the highest grades available from commercial suppliers.

Animals—C3H/HeN mice were obtained from Charles River (Kingston, N.Y.). Mice of the endotoxin-resistant C3H/HeJ strain were obtained from Jackson Laboratories (Bar Harbor, Me.).

Cell Culture—The mouse macrophage cell line RAW 264.7 and the cachectin/TNF sensitive cell line L929 were obtained from American Type Culture Collection (Rockville, Md.) and maintained in RPMI 1640 or Dulbecco's modified MEM ((DMEM) GIBCO, Grand Island, N.Y.), respectively. Both media were supplemented with 20 mM Hepes and 10% fetal bovine serum (Hyclone, Logan, Utah). For the production of stimulated RAW 264.7 supernatants, cells were grown in 150 mm tissue culture dishes (Falcon) in RPMI plus 10% fetal bovine serum until they reached confluency. The cells were washed five times in Hanks' balanced salt solution and the medium was replaced with serum-free RPMI supplemented with 1 $\mu$g/ml of lipopolysaccharide (LPS W, *E. coli* 0127:B8, Difco, Detroit, Mich.). The cells were incubated at 37° C. for 16–18 hours and the supernatants filtered through 0.22 $\mu$m filters.

Purification of MIP-1—One to five liters of supernatant mediator substance were concentrated 16–40-fold in a DC2 hollow fiber concentration system with a 10,000 dalton molecular weight cutoff (Amicon Corp., Lexington, Mass.) and diafiltrated against 6 liters of 20 mM Tris buffer, pH 8.0, using the same device. Octyl glucoside was added to the concentrated, diafiltrated supernatant to a final concentration of 1% (w/v) and the mixture was applied to a MONO Q 10/10 (anion exchange (Pharmacia, Rahway, N.J.)) column previously equilibrated with 20 mM Tris buffer, pH 8.0, and connected to a fast protein liquid chromatography (FPLC, Pharmacia) apparatus. A linear gradient of 114 ml (total volume) from 0 to 1M NaCl in the same buffer (and a flow rate of 2 ml/min.) was used for elution.

Samples of each fraction were subjected to polyacrylamide gel electrophoresis in a denaturing system containing sodium dodecyl sulfate (SDS-PAGE) in 10–15% or 10–18% linear gradient slab gels under reducing conditions. Molecular weight standards (BRL, Inc., Bethesda, Md.) were run in parallel. Fractions containing MIP-1 eluted in the same region as cachectin/TNF and were easily recognized as a characteristic doublet of approximately 8,000 molecular weight.

Peak MIP-1 -containing fractions (as assessed by SDS-PAGE and silver staining) were pooled, concentrated and fractionated on a high-performance gel-filtration column (SUPEROSE gel filtration medium 12; Pharmacia) previously equilibrated with 100 mM ammonium acetate. MIP-1 was recovered in the void volume of the column and was greater than 95% pure as judged by SDS-PAGE and silver staining. MIP-1 purified in this manner contained approximately 0.2 ng LPS/μg MIP-1.

Heparin Chromatography—Heparin-conjugated SEPHAROSE (Pharmacia) was used to assay the ability of MIP-1 to bind heparin. A C10/20 column (Pharmacia) packed with 8 ml of gel was attached to an FPLC apparatus and equilibrated with 20 mM Tris, pH 8.0. Two ml of 12-fold concentrated and diafiltrated RAW 264.7 supernatant (as above) was applied to the column and a linear gradient of 0 to 2M NaCl in the same buffer was used for elution.

Chromatofocusing—Eight micrograms of a peak MIP-1-containing fraction from MONO Q chromatography was equilibrated in 25 mM bis-Tris plus 10% betaine (w/v), pH 7.1, and applied to a MONO P column previously equilibrated in the same buffer. Protein was eluted with a linear gradient of POLYBUFFER 74 pH gradient buffer (Pharmacia) (1:10 in double-distilled water) with 10% betaine (pH 4.0), resulting in a descending pH gradient ranging from 7 to 4.

Protein Assay—Protein content was measured by an assay (Bradford, M., ANAL. BIOCH. 72:248–254, (1976)) using BSA as a standard (Bio-Rad. Richmond, Calif.).

Endotoxin Assay—Endotoxin levels were determined using a chromogenic limulus assay (Whittaker M.A. Bioproducts, Walkersville, Md.) according to the instructions of the manufacturer.

Protein Sequencing—Purified MIP-1 was sequenced by the Rockefeller University protein sequencing facility. The Dayhoff protein sequence bank was searched for homologous amino acid sequences using the computer program d-FAST-P.

In Vivo Inflammatory Activity—Polymorphonuclear leukocyte (PMN) infiltration was evaluated using footpad injections, according to Granstein, R. D., et al., J. CLIN. INVEST. 77:1020–1027 (1986). Briefly, female C3H/HeJ mice (6–12 weeks) were lightly anesthetized with phenobarbital (25 mg/kg body weight, i.p.). Animals were randomized to receive a subcutaneous footpad injection of 0.05 ml containing $10^{-10}$ moles N-formylmethionylleucylphenylalanine (fMLP); 10, 100 or 1000 ng of recombinant human IL-1α or recombinant human cachectin/TNF; or 1, 10, 100, or 1000 ng of murine MIP-1 (purified as above) in RPMI 1640 with 0.1% fetal bovine serum. RPMI 1640 with 0.1% fetal bovine serum alone served as a control. In some cases, mice received the test substance in one hind-limb foot-pad and the control carrier in the contralateral hindlimb. In other cases, a randomized block design was employed. Mice were sacrificed four hours following injection and hindlimbs were fixed in 10% buffered formalin. Hind-limbs were decalcified, embedded in paraffin and thin-sections of footpads were stained with hematoxylin and eosin.

In Vitro PMN Migration Assays—Heparinized venous blood was obtained from healthy volunteers. Leukocytes containing greater than 95% PMN's as judged by cell sorter analysis were isolated by Ficol-HYPAQUE density gradient centrifugation and dextran sedimentation (Klempner, M. S., et al., J. CLIN. INVEST. 64:996–1002 (1979)). Residual erythrocytes were removed by lysis with hypotonic saline. Cells were resuspended in Gey's balanced salt solution (GBSS, pH 7.4) and 2% bovine serum albumin (BSA) to a final concentration of $2.5 \times 10^6$ cells/ml.

In vitro chemokinesis was assayed using a modification of the technique described by Boyden (Boyden, S. V., J. EXP. MED. 115:453–466 (1962)). Bottom wells of blind well chambers were filled with 25 μl of buffer containing the test compound, i.e. fMLP ($10^{-8}$M), MIP-1 or buffer alone; and the top wells filled with 45 μl of GBSS/BSA containing $1.1 \times 10^4$ PMN's. The two wells were separated by a cellulose nitrate membrane with a 3 μm pore size (SM 11302, Sartorius, Westbury, Conn.). Chambers were incubated at 37° C. in a humidified 5% $CO_2$-95% room air chamber for 45 minutes. Membranes were removed and stained according to a previously described protocol (Hesse, D. G., et al., J. CLIN. INVEST. 73:1078–1085 (1984)). The number of PMN's migrating into the membrane was counted for every 10 μM up to 130 μM using an automated Optomax imaging system (Optomax, Inc., Hollis, N.H.). Migration was quantitated in three randomly selected fields for each membrane with each sample tested in triplicate. Chemokinesis was defined as the mean distance migrated into the membrane (expressed as a percent) compared to GBSS alone (0%) and that of the positive fMLP control (100%).

Chemokinetic data are expressed as percents (mean±standard error of the mean (SEM)) of the control chemokinetic response. A one-way analysis of variance (ANOVA) was used to compare the response to MIP-1 with that to GBSS alone in the bottom well of the chamber.

Induction of Hydrogen Peroxide Release—The ability of MIP-1 to elicit the release of $H_2O_2$ from adherent human PMN or monocytes was tested by the method recently described in detail. In brief, PMN and mononuclear leukocytes in heparinized or citrated blood were isolated in Neutrophil Isolation Medium (Packard Instrument Co., Downer's Grove, Ill.), washed and plated separately at $1.5 \times 10^4$ PMN or $2 \times 10^5$ mononuclear cells per well in flat-bottomed, 6-mm diameter polystyrene tissue culture wells that had previously been coated with fetal bovine serum and extensively washed. The assay mixture contained 2.4 nM scopoletin, 0.5 μg horseradish peroxidase, 1 mM sodium azide and the indicated test agents in a final volume of 0.13 ml of Krebs-Ringer phosphate buffer with glucose at 37° C. Loss of fluorescence of scopoletin due to oxidation by $H_2O_2$ was recorded at 15- or 30-minute intervals in a plate-reading fluorometer and converted to nM $H_2O_2$ by microcomputer (de la Harpe, J., et al. , J. IMMUN. METHODS 78:323–336 (1985)).

IL-1 and Cachectin/TNF Bioassays—MIP-1 was assayed for IL-1 activity by its ability to stimulate C3H/HeJ thymocytes to undergo blastogenesis in the presence of suboptimal quantities of phytohemagglutinin, as previously described (Moldawer, L. L., et al., J. IMMUN. 138:4270–4274 (1987)).

Cachectin/TNF activity was assayed by its ability to kill actinomycin D-treated L929 murine fibroblasts (Ostrove, J. M., et al., PROC. SOC. EXP. BIOL. MED. 160:354–358 (1979)). Approximately 50,000 L929 cells were plated in each well of a 96-well plate (Falcon) in DME medium containing 1 μg/ml actinomycin D and increasing quantities of MIP-1. After 14–16 hours, the chromogen (3-(4,5-dimethylthiazol2-yl)-2,5-diphenyl tetrazolium bromide (MTT)) was added and the cells incubated for an additional 4 hours. Cell viability was assessed by the ability of the cells to reduce the chromogen during this time period by a modification of a known procedure (Mosmann T., J. IMMUN. METHODS 65:55–63 (1985)). The medium was aspirated and the cells lysed with 0.04N hydrochloric acid in isopropanol. After addition of one volume double-distilled water, the extent of chromogen reduction was measured by reading the plates at O.D. 570/690 using an automated ELISA-plate reader and values were compared to a standard cytotoxicity curve obtained in like manner with recombinant human cachectin/TNF.

Cachectin/TNF was also assayed by the suppression of lipoprotein lipase on 3T3-L1 cells as previously described (Beutler, B., et al., J. EXP. MED. 161:984–995 (1985)). The ability of MIP-1 to induce cachectin/TNF in primary cultures of macrophages was assessed by eliciting macrophages with an i.p. injection of two milliliters of sterile thioglycollate broth (DIFCO) and collecting the cells 4 to 6 days later by peritoneal lavage. The cells were washed and resuspended in serum-free RPMI and plated at $10^6$ cells/well in 24-well tissue culture plates. Test substances (LPS, 0.0001–1 μg/ml; MIP-1, 1 μg/ml) were added and the cells incubated at 37° C. for 18 hours. The cell-free supernatants were collected and assayed for cachectin/TNF activity by cytotoxicity on L929 cells as described above.

Purification of MIP-1α and MIP-1β: MIP-1 containing fractions from high performance gel filtration chromatography over SUPEROSE 12 were pooled, concentrated using a PM-10 membrane in a stirred cell (Amicon Corp., Danvers, Mass.), and diafiltrated against 0.01M sodium phosphate buffer, pH 6.4. Two components of MIP-1 were then resolved by SDS-hydroxylapatite chromatography according to a known procedure (Moss, B. and E. N. Rosenblum., J. BIOL. CHEM., 247:5194, (1972)). In brief, a 500 μg aliquot of MIP-1 was equilibrated in 0.01M sodium phosphate buffer, pH 6.4, containing 1% SDS and 1% mercaptoethanol and placed in a boiling water bath for 2 minutes. The sample was immediately diluted 10-fold with 0.01M sodium phosphate buffer (pH 6.4) containing 0.1% SDS and 1.0 mM DTT (Buffer A), applied directly to a hydroxylapatite column (Bio Gel HPHT, Bio-Rad, Richmond, Calif.) pre-equilibrated in Buffer A. A 25 ml linear gradient from 0.01M to 0.35M sodium phosphate buffer (pH 6.4) containing 0.1% SDS and 1.0 mM DTT was used for elution.

Protein Sequencing: N-terminal amino acid sequence analysis of MIP-1α and MIP-1β were performed on an Applied Biosystems gas phase sequenator. The Dayhoff protein sequence bank was searched for homologous amino acid sequences using the computer program d-FAST-P.

Hydropathicity Plots: The hydropathicity plots of MIP-1α and MIP-1β were calculated by a modification of a known algorithm (Hopp, T. P. and K. R. Woods., PROC. NATL. ACAD. SCI. U.S.A. 78:3824 (1981)).

Construction of cDNA Library: A cDNA library from LPS-stimulated RAW 264.7 cells was obtained as described previously (Davatelis, G., S. D. Wolpe, C. Luedke, P. Tekamp-Olson, J. Merryweather, K. Hermsen, C. Gallegos, D. Coit,.and A. Cerami, J. EXP. MED. In press (1988)). In brief, confluent monolayers of RAW 264.7 cells were washed five times in HBSS and covered with serum-free RPMI 1640 culture medium containing 1.0 μg/ml LPS. After incubation at 37° C. for 2 hours, total RNA was extracted into 6M guanidinium thiocyante (Ullrich, A., J. Shine, J. Chirgwin, R. Pictet, E. Tischer, W. J. Rutter, and H. M. Goodman, SCIENCE 196:1313 (1977)). Poly(A)+ RNA was then isolated by two cycles of oligo(dT)-cellulose chromatography according to a modification of a known procedure (Maniatis, T., E. F. Fritsch, and J. Sambrook, "Molecular Cloning. A Laboratory Manual." Cold Spring Harbor Laboratory, Cold Spring Harbor, N.Y. p. 197 (1982)). Double-stranded cDNA was prepared from the poly(A)+ selected RNA according to a known procedure (Gubler, U., and B. J. Hoffman, GENE. 25:263 (1983)). Internal Eco R1 sites were methylated, Eco R1 linkers added, and the cDNA inserted into the Eco R1 sites of bacteriophage lambda gt10 (Huynh, T. V., R. A. Young, and R. W. Davis, DNA Cloning: A Practical Approach, D. M. Gloves, ed., IRL Press, Oxford. 149 (1985)).

Construction of the Probe Pools: Two oligonucleotide probe pools corresponding to the "major" sequence were synthesized according to a known procedure against amino acids #22–30 of a partial amino-terminal sequence. This portion of the polypeptide was selected because of its lower degeneracy in the codon dictionary when compared to the remainder of the sequence. The resulting probe pools are two 512-fold degenerate pools of 26 nucleotides in length.

An oligonucleotide probe pool corresponding to the "minor" amino acids 2–8 of a partial N-terminal sequence of MIP-1α were synthesized as described by a modification of a known method (Warner, B. D., M. E. Warner, G. A. Karns, L. Ku, S. Brown-Shimer, and M. S. Urdea, DNA. 3:401 (1984). This particular sequence was chosen because it was the region of least apparent homology between MIP-1α (major) and MIP-1β (minor) sequences.

Screening of the Library: In regard to MIP-1α, nitrocellulose filter lifts of a low-density plating ($5 \times 10^3$ pfu/plate) of the library were hybridized using the synthetic probe pool that had been 5'-end labeled with $^{32}$P-ATP (New England Nuclear, Boston, Mass.). Following the hybridization, the lifts were washed using the method of Wood et al. (10). After several rounds of screening, 18 recombinant phage clones were isolated and grown in bulk for DNA isolation.

In regard to MIP-1β, duplicate nitrocellulose filter lifts of the plated library ($4 \times 10^5$ plaques) were hybridized overnight at 42° C. in 4×SSC, 2×0 Denhardt's solution, 40 mM sodium phosphate buffer, pH 7.0, 0.3 mg/ml sonicated salmon sperm DNA, 0.1% SDS and $2.5–5 \times 10^4$ cpm/ml/degeneracy of the $^{32}$P-ATP 5'end-labeled synthetic oligonucleotide probe pool. Following hybridization, the filters were washed; the final washes were done under conditions of moderate stringency: 2×SSC, 0.1% SDS at 50° C. Plaques which were positive on duplicate filters were subjected to a second round of low density plating and screening. In this way two independent positive phage clones were isolated from which DNA was prepared for further analysis.

DNA Sequence Analysis: The cDNA inserts to be analyzed were subcloned into M13 phage vectors and DNA sequencing was performed by the dideoxy-chain termination method of Sanger et al. (F. Sanger and S. Nicklen, R. Coulson, PROC. NATL. ACAD. SCI. U.S.A. 74:5463 (1977)).

Blot Hybridization Analysis—Northern blot hybridization was performed by an adaptation of a known method (Lehrach, H., D. Diamond, J. M. Wozney, and H. Boedtker, BIOCHEMISTRY. 16:4743 (1977)). Total RNA of LPS-stimulated and nonstimulated RAW 264.7 cells were electrophoresed through 1.2% agarose gels and transferred to nitrocellulose filters.

Primer Extension—The synthetic oligonucleotide primer was end labeled using [τ-$^{32}$P]ATP (3,000 Ci/mmol, Amersham Corp., Arlington Heights, Ill.) and the T4 polynucleotide kinase. The primer extension method was a modification of a known method (Walker, M. D., T. Edlund, A. M. Boulet, and W. J. Rutter, NATURE LOND. 306:557 (1983)).

RESULTS

Figure 1A:
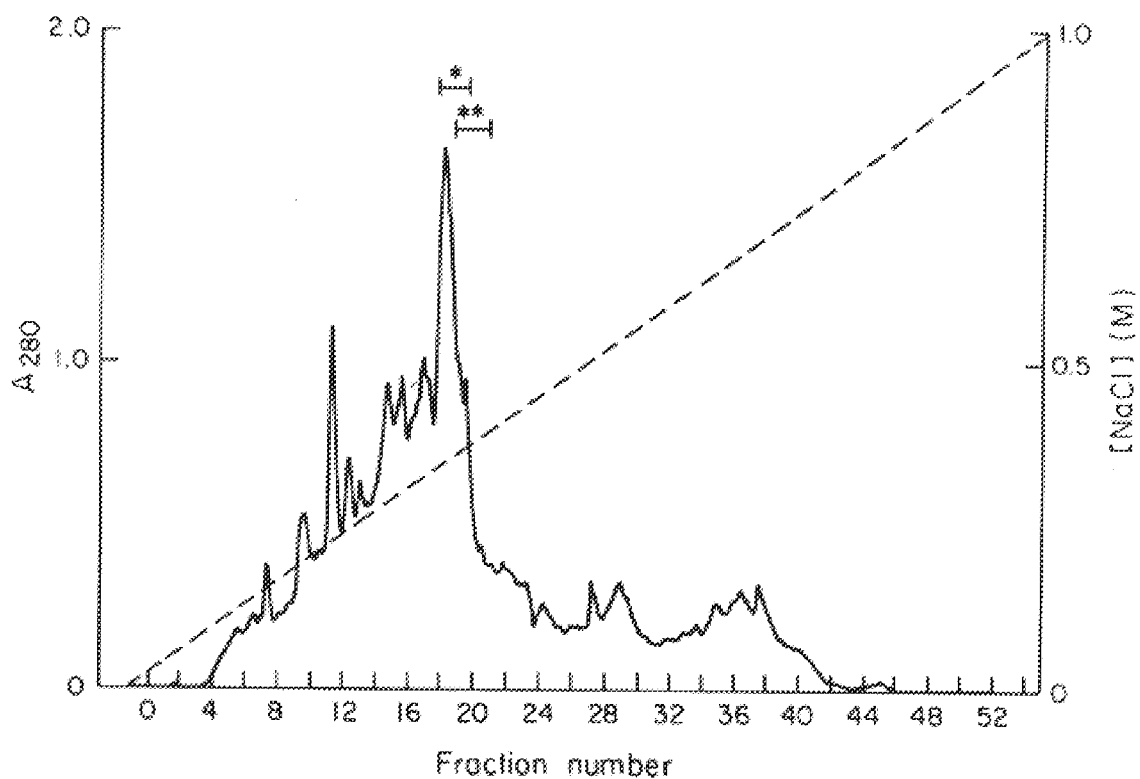

Purification of MIP-1—When supernatants of stimulated RAW 264.7 cells were fractionated by MONO Q (anion exchange) chromatography, MIP-1 was apparent as a distinctive doublet of about 8,000 daltons on SDS-PAGE after silver staining (FIG. 1). MIP-1 reproducibly eluted within a fraction or two of cachectin/TNF at approximately 0.37M NaCl and appeared to be produced in approximately the same quantities as judged by silver-staining.

Chromatofocusing revealed that MONO Q-purified MIP-1 eluted at a slightly more acidic pH than cachectin/TNF. This corresponded to a pI of 4.6 (not shown).

Figure 2B:
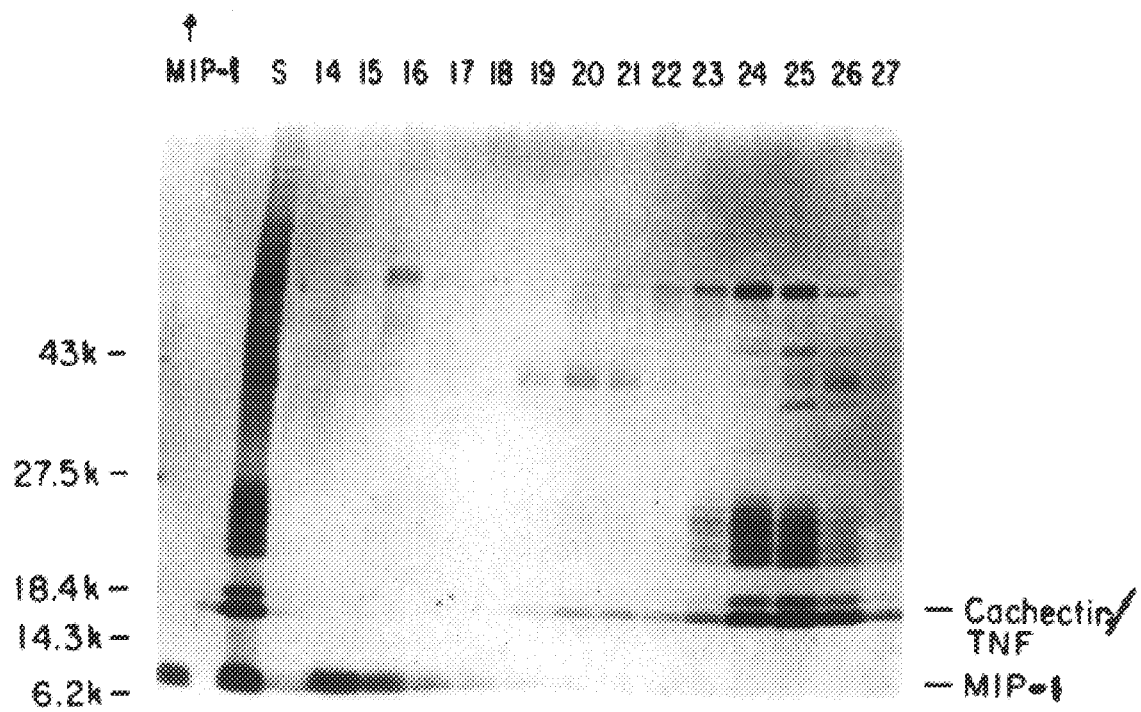
FIG. 2 is a combined graphical and electrophoretic gel depiction of further gel separation and purification of the present inflammatory cytokine. Peak MIP-1 containing fractions from MONO Q anion exchange column were concentrated to 200 μl and applied to a Superose 12 column equilibrated with 100 mM ammonium acetate. MIP-1 (*) eluted in the void volume, well separated from cachectin/TNF (**). The insert shows a 10–18% SDS-PAGE gel to which 50 μl aliquots from the indicated fractions have been applied. The dagger indicates purified MIP-1 used as a marker.
Figure 2A:
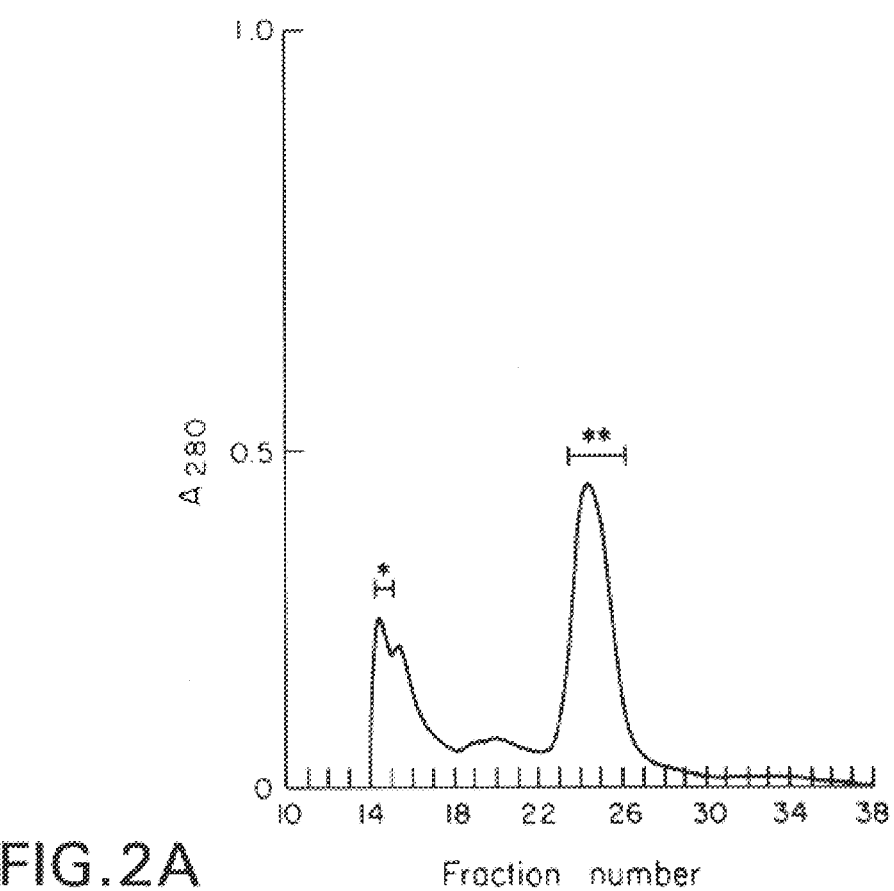

In order to further purify MIP-1, advantage was taken of its tendency to aggregate. Aggregation of MIP-1 was observed to occur during the concentration of the crude material and before diafiltration or fractionation on MONO Q (data not shown). When fractionated by gel filtration in phosphate-buffered saline, MIP-1 formed multimers of various molecular weights ranging from approximately 20,000 daltons to material eluting in the void volume ($\geq 2 \times 10^6$ daltons; data not shown). In 100 mM ammonium acetate this tendency was exaggerated and the majority of the protein eluted in high molecular weight fractions (FIG. 2). Under these conditions, MIP-1 of greater than 95% purity, as judged by SDS-PAGE and silver staining, was obtained.

Partial N-terminal amino acid sequence data of purified MIP-1 (FIG. 3) showed a single major sequence although sequences of two separate batches showed consistent minor amino acids at several specific positions in the N-terminal region. Computer-based analysis of this sequence data revealed no significant homology with any previously described protein.

Figure 4B:
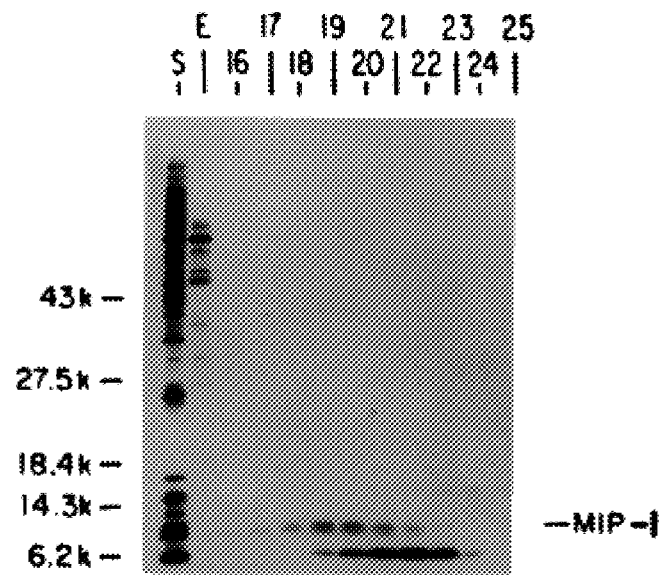
FIG. 4 is a combined graphical and electrophoretic gel depiction of the binding and elution of the inflammatory cytokine of the present invention to heparin. Two ml of 12-fold concentrated and diafiltrated LPS-stimulated RAW 264.7 supernatant were applied to a heparin-SEPHAROSE agarose gel filtration medium column and eluted with a linear gradient of 0 to 2M NaCl in 0.02M Tris-HCl buffer, pH 7.8. Two major peaks were observed; MIP-1 (*) eluted in the second peak, corresponding to 0.6–0.75M NaCl. The insert shows a 10–18% acrylamide gradient SDS-PAGE gel to which 50 μl aliquots from the indicated fractions have been applied.
Figure 4A:
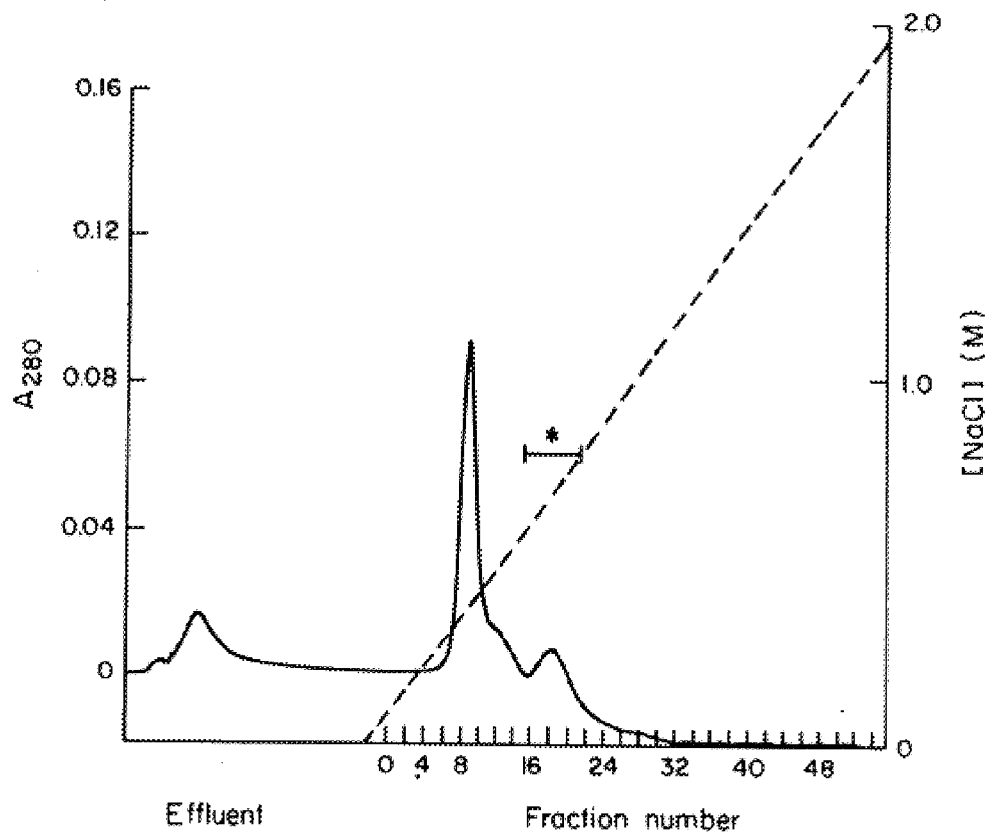

Affinity of MIP-1 for Heparin—During the purification of MIP-1, its affinity for heparin (FIG. 4) was noted. When 2 ml of 12-fold concentrated RAW 264.7 supernatant were applied to a column and eluted with a linear gradient of 0 to 2M NaCl, MIP-1 was one of two major proteins detectable by SDS-PAGE and silver staining, eluting at approximately 0.7M NaCl.

Determination of Biological Activities—At concentrations as high as 20 µg/ml, purified MIP-1 did not stimulate blastogenesis of C3H/HeJ thymocytes. Recombinant human IL-1, on the other hand, was active in this assay at concentrations as low as 10 pg/ml (data not shown). Similarly, purified MIP-1 did not kill L929 cells in the presence of actinomycin D even at concentrations of 1 µg/ml whereas recombinant human cachectin/TNF was able to induce killing at concentrations as low as 15 pg/ml (data not shown). Further, purified MIP-1 did not induce down-regulation of lipoprotein lipase in 3T3-L1 cells (data not shown). At 1 µg/ml, purified MIP-1 did not induce cachectin/TNF production by primary thioglycollate-elicited mouse macrophages in the presence of 10 µg/ml polymyxin B (data not shown).

Figure 5:
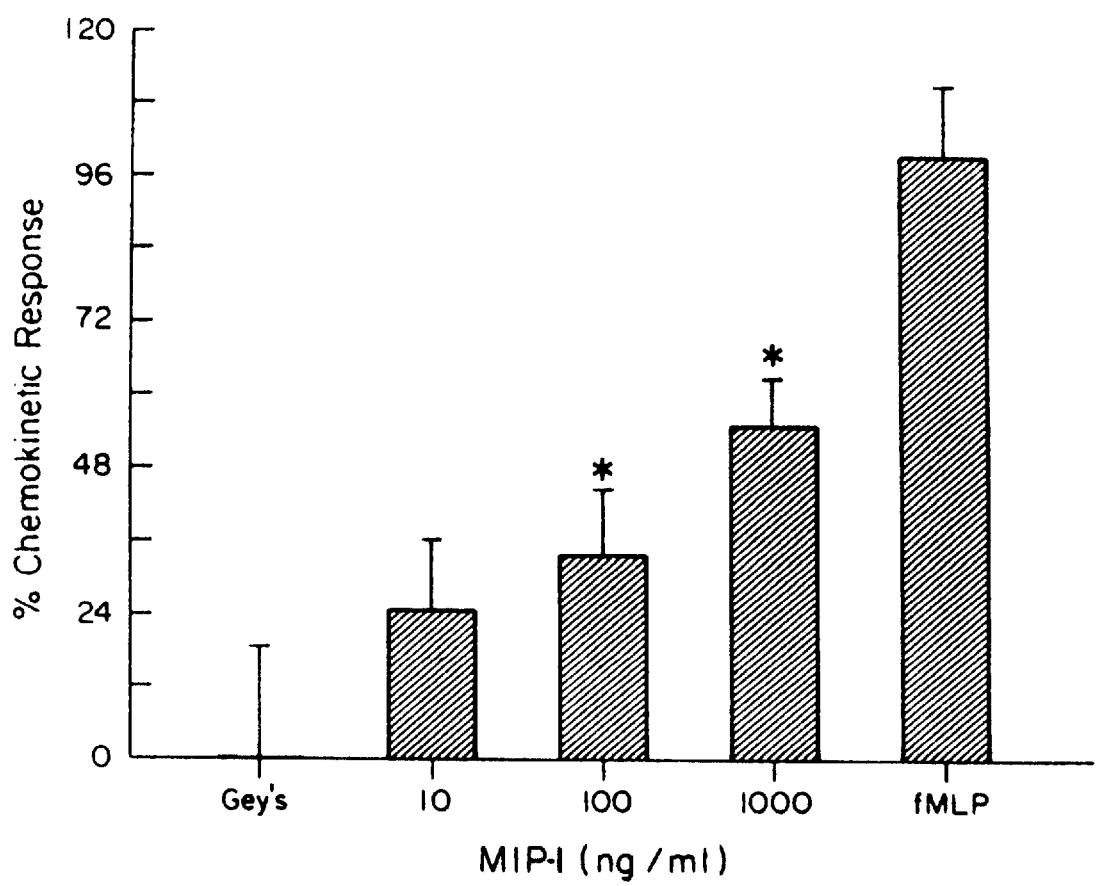
FIG. 5 is a photomicrograph of C3H/HeJ footpads fixed 4 hours following subcutaneous injection of the inflammatory cytokine of the present invention with controls and comparative injections of cachectin/TNF. Tissues were fixed in buffered formalin and stained with hematoxylin-eosin. Magnification is 400×. Plate A—Sham injections reflecting normal histology. Plate B—100 ng MIP-1: moderate infiltration of neutrophils and mast cells. Plate C—100 ng cachectin/TNF: moderate infiltration of neutrophils. Plate D—$10^{-10}$ moles fMLP: extensive infiltration with some focal necrosis.

Although free of the above-mentioned IL-1-and cachectin/TNF-like activities, MIP-1 did induce a localized inflammatory response at four hours when injected subcutaneously into the footpads of C3H/HeJ mice. Maximal inflammation occurred when 100 ng of MIP-1 were administered and was characterized primarily by PMN leucocyte infiltration (FIG. 5, plate A). The control response to an injection of carrier is shown in plate B. The degree of neutrophil infiltration seen with MIP-1 was not as marked as that seen when $10^{-10}$ moles of fMLP were administered (FIG. 5, plate C). However, the degree of neutrophil infiltration was comparable to that observed with 10 ng of recombinant cachectin/TNF. Recombinant human IL-1 elicited no inflammatory responses at four hours when administered at these doses (data not shown).

Figure 6:
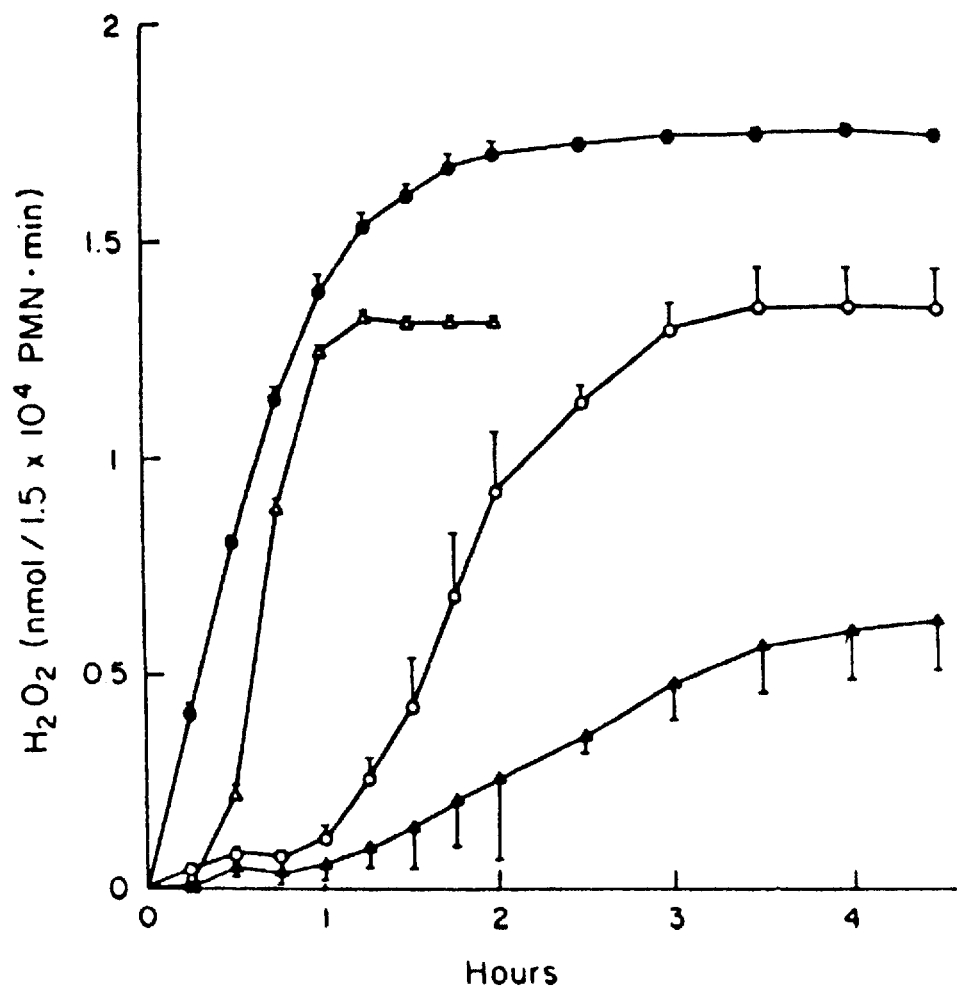
FIGS. 6 graphically depicts the results of tests for the induction of neutrophil chemokinesis by the inflammatory cytokine of the present invention. Data represent the mean percent of the control migratory response of five experiments. Values are presented as the percent increase in neutrophil migration relative to the Gey's basic salt solution negative control (0%) and the $10^{-8}$M fMLP positive control (100%). *=concentrations of MIP-1 showing significant increases in the percent chemokinetic response versus GBSS alone (p<0.01 by ANOVA).

MIP-1 induced chemokinesis in human neutrophils in vitro. Data presented in FIG. 6 represent the mean per cent of the control migratory response of five experiments. Values are presented as the percent increases in neutrophil migration relative to the negative GBSS (0%) and positive fMLP $10^{-8}$M controls (100%). At concentrations equal to or greater than 100 ng/ml, MIP-1 elicited a significant increase in neutrophil migration (p<0.01 by ANOVA). Inclusion of polymyxin B (10 µg/ml) had no effect on MIP-1-induced chemokinesis. Further, LPS at concentrations of 10–1000 ng/ml was not active in this assay (data not shown).

Recombinant cachectin/TNF, but not rIL-1α, triggers a delayed but significant respiratory burst in human PMN, provided the cells are adherent to a surface coated with serum or extracellular matrix proteins. Similarly, MIP-1 at >1 µg/ml triggered adherent PMN to release $H_2O_2$ in four experiments, one of which is illustrated in FIG. 7. Compared to cachectin/TNF tested in parallel cultures, the response to MIP-1 was more delayed (60 minute lag versus 15 minute lag for cachectin/TNF), and the maximal sustained rate was lower (1.2 nmol/min per $10^6$ PMN versus 3.0 for cachectin/TNF and 2.1 for PMA). However, the duration of the response was greater (2.5 hours compared to 1 hour for cachectin/TNF) and thus, the total amounts of $H_2O_2$ released were similar. Because MIP-1 binds heparin, experiments were also performed with PMN isolated from citrated rather than heparinized blood and gave similar results. Neither MIP-1 (not shown) nor cachectin/TNF triggered $H_2O_2$ release from monocytes.

DISCUSSION

The data presented above indicate that, while the inflammatory cytokine MIP-1 bears no significant sequence homology to any previously described protein, it shares some of the overlapping properties typical of inflammatory mediators such as cachectin/TNF and IL-1.

MIP-1 was isolated on the basis of its interesting physical properties. As indicated earlier, although MIP-1 migrates as a doublet of about 8,000 daltons on SDS-PAGE, it readily forms high molecular weight aggregates in excess of $2 \times 10^6$ daltons as judged by gel filtration. Partial amino acid sequence data show one "major" sequence with "minor" substitutions at several positions.

The binding of MIP-1 to heparin under conditions where the protein is anionic suggests a specific interaction. This is further emphasized by the observation that MIP-1 is one of two major macrophage-secreted proteins that bind to heparin at high salt concentrations. It is possible that MIP-1 may play a role in the coordination of the inflammatory activities of macrophages, mast cells and neutrophils. MIP-1 may also interact with basement membrane proteoglycans during inflammation.

The findings presented here are consistent with the suggestion that either cachectin/TNF or MIP-1 are capable of inducing an inflammatory response. Cachectin/TNF has previously been shown to induce neutrophil chemokinesis (Figari, I. S., et al. 1987, BLOOD (in press); and Ming, W. J., et al., J. IMMUN. 138:1469–1474 (1987)) as well as activation (Shalaby, M. R., J. IMMUN. 135:2069–2073 (1985); and Tsujimoto, M., et al., BIOCH. BIOPHYS. RES. COMMUN. 137:1094–1100 (1986)). In the present study MIP-1 was shown also to be capable of inducing neutrophil chemokinesis. In addition, at the doses used here, cachectin/TNF and MIP-1 each elicited similar degrees of inflammation in vivo. Although others have shown that recombinant IL-1 can induce an inflammatory reaction in vivo (Granstein, R. D., et al., J. CLIN. INVEST. 77:1020–1027 (1986)), no such effect was found here; it is possible that the recombinant human IL-1α used here is less active in this regard than the murine IL-1α used in published experiments (Granstein, R. D., et al., J. CLIN. INVEST. 77:1020–1027 (1986)).

It is unlikely that the effects of MIP-1 administration are due to cachectin/TNF contamination as there was no cachectin/TNF bioactivity detected by L929 cytotoxicity assay at the doses used. Further, MIP-1 did not induce primary thioglycollate-elicited macrophages to produce cachectin/TNF. Endotoxin contamination was ruled out as an explanation for the chemokinetic effect, as chemokinesis was not affected by the presence of polymyxin B; and LPS itself, at concentrations greater than were present in the MIP-1 assays, had no chemokinetic effect.

The inflammation induced by MIP-1 was observed in mice of the endotoxin-resistant C3H/HeJ strain using preparations with low levels of endotoxin contamination (0.2 ng LPS/µg MIP-1).

As described previously, native murine MIP-1 is isolated as a doublet with nearly identical subunit molecular weights of approximately 8000 daltons. Although two MIP-1 components are separated to some extent by SDS-PAGE, their electrophoretic mobilities are so similar that preparative SDS-PAGE appeared an impractical means of purification. Native MIP-1 (doublet) was subjected to SDS-hydroxylapatite chromatography, a technique which has been used successfully to separate protein subunits of similar electrophoretic mobility (B. Moss and E. N. Rosenblum, J. BIOL. CHEM. 247:5194 (1972)). As can be seen in FIG. 13, two distinct protein peaks are observed following fractionation of native MIP-1 on a hydroxylapatite column in the presence of SDS. The first peak elutes at 0.24M sodium phosphate and the second peak elutes at 0.27M sodium phosphate. SDS-PAGE analysis of the column fractions revealed that the first peak corresponded to the lower molecular weight band of MIP-1 now referred to as MIP-1α, while the second peak corresponded to the higher molecular weight band referred to as MIP-1β. Using this technique, each component was obtained in pure form (>95% as judged by SDS-PAGE) for N-terminal amino acid sequence analysis.

To elucidate the molecular structure of murine MIP-1α, a cDNA clone was isolated containing the sequence coding for MIP-1α. As a first step, the mouse macrophage cell line RAW 264.7 was stimulated with LPS. Since RAW 264.7 cells have been shown to be a source of MIP-1α protein after LPS stimulation, the MIP-1α mRNA was expected to be highly reiterated in these LPS-induced cells.

Poly(A) +RNA was prepared from total RNA by two cycles of lambda oligo-dT-chromatography and a cDNA library was constructed in lambda gt10. The cloning efficiency was $10^6$ clones/µg of poly(A) +RNA. The library was amplified and shown to contain inserts of greater than 1,000 bp in above 60% of recombination plaques. Nitrocellulose filter lifts of a low-density plating of the library were screened using two synthetic oligonucleotide pools that were based on the partial $NH_2$-terminal amino acid sequence of purified MIP-1 (S. D. Wolpe, G. Davatelis, B. Sherry, B. Beutler, D. G. Hesse, H. T. Nguyen, L. L. Moldawer, C. F. Nathan, S. F. Lowrey, and A. Cerami, J. EXP. MED. 167:570 (1987)). Each pool consisted of a 512-fold degeneracy pool 26 nucleotides in length (FIG. 9).

After the initial library screening, positive plaques were streaked onto fresh bacterial lawns and a secondary screening was performed by differential plaque hybridization. Replicate lifts of the secondary streaks were hybridized to either $^{32}$P-labeled pool #1 or pool #2. Since the melting temperature (T) of DNA/DNA hybrids can be approximated by the empirical formula: $T=16.6(\log[Na+]+0.41(\%[G+C])+81.5-500/\text{number of bp in homology}$, one of the probe pools was effectively eliminated through the differential melting temperatures of the hybrids based on a 26-bp homology. By using a tetramethylammonium chloride washing technique (W. Wood, I. J. Gitschier, L. A. Laskey, and R. M. Lawn, PROC. NATL. ACAD. SCI. USA. 82:1585 (1985)), which abolishes the preferential melting of A-T vs. G-C base pairs, the melting temperature (Tm) becomes dependent simply on the length of the hybrid.

After several rounds of differential hybridization, probe pool #1 yielded 18 recombinant phage clones out of $10^4$ screened that hybridized under maximally stringent conditions for MIP-1α. All of the plaques were purified and DNA was prepared from each. The recombinant phage clone 52 appeared to contain the largest cDNA Eco-RI insert of about 750 bp and was chosen for further characterization. The complete nucleotide sequence of cDNA clone 52, as well as 262 bp of 5' sequence of another, partially overlapping clone, 32, have been determined and are shown in FIG. 10. The latter clone, which was isolated in a later screening, had a smaller Eco RI insert than clone 52, but a larger 5'-end fragment and therefore presumably less poly(A) tail. The MIP-1α nucleotide sequence of 763 bp predicts a single open reading frame starting at nucleotide 2. The mature protein sequence, starting at position one, is 69 amino acids in length and comprises the "major" sequence previously defined by $NH_2$-terminal analysis of the purified MIP-1 protein (S. D. Wolpe, G. Davatelis, B. Sherry, B. Beutler, D. G. Hesse, H. T. Nguyen, L. L. Moldawer, C. F. Nathan, S. F. Lowrey, and A. Cerami, J. EXP. MED. 167:570 (1987)).

The first methionine present in the sequence is found at position −23. This is postulated to be the initiating methionine for the MIP-1α precursor based on the following observations. Structural analysis of the putative presequence (−23 to −1) indicates that it has features characteristic of typical signal sequences (i.e., α-helix and a hydrophobic core (D. Perlman and H. O. Halvorson, J. MOLE. BIOL., 167:391 (1983)). The predicted initiating ATG has a purine at relative position −3, which has been shown (M. Kozak, CELL. 44:283 (1986)) to have a dominant effect on translation imitation efficiency. Furthermore, in a survey of the frequency of A,C,T,G around the translation start site of 699 vertebrate mRNAs, 97% had a purine at position −3, 61% having an A at that position (M. Kozak, NUCLEIC ACIDS RES. 15:8125 (1987)). NA clone. oligonucleotide primer (FIG. 10) was hybridized to LPS-stimulated RAW 264.7 poly(A) +RNA and elongated with reverse transcriptase. After hybridization, an extended primer of 98±2 nucleotides was obtained (data not shown). After subtracting out the primer length of 25 nucleotides and the sequence 5' to the primer we had previously determined (61 nucleotides), one can conclude that the known sequence is 10–14 nucleotides short of a full-length cDNA. While it is possible than an in-frame AUG is present in this cloned region, it seems highly unlikely given that only 14 of 346 sequenced vertebrate mRNAs have 5' noncoding sequences less than 19 nucleotides in length ((M. Kozak, NUCLEIC ACIDS RES. 15:8125 (1987)). It can then be estimated that the 5' untranslated sequence is about 82 nucleotides, well within the 20–100 nucleotide length of most vertebrate 5' noncoding regions sequenced to date.

The proposed pre-MIP-1α is 92 amino acids in length. There are no consensus Asn-X-Ser,Thr sites for N-linked glycosylation evident in the molecule. There are 7 cysteines, 3 in the presequence and 4 in the mature sequence. The codon usage of the putative pre-MIP-1α agrees well with that determined for 66 other sequenced murine genes (T. Marayama, T. Gojobori, S. Aota, and T. Ikemura, NUCLEIC ACIDS RES. 14(Suppl):r151 (1986)). The peptide has no significant sequence similarity to any protein as defined to date by the d-fast-P program homology search (D. J. Lipman and W. R. Pearson, SCIENCE, 227:1435, (1985)) of the Dayhoff protein data base. The DNA sequence was also compared against GenBank genetic sequence data with a similar negative result.

In the 3'-untranslated region, there is a single consensus polyadenylation site at bp 711 to 716. There are also 4 sequences that have only one mismatch to a known cytokine consensus 3'-untranslated sequence (Copending application Ser. No. 017,360, filed Feb. 24, 1987, the disclosure of which is incorporated herein by reference. See also, D. Caput, B. Beutler, K. Hartog, R. Thayer, S. Brown-Shimer, and A. Cerami, PROC. NATL. ACAD. SCI, 83:1670 (1986) ). The 3'-untranslated consensus cytokine sequence (TATT)$_n$ is also present (R. Reeves, A. G. Spies, M. S. Nissen, L. D. Buch, A. D. Weinberg, P. J. Barr, N. S. Maguuson and J. A. Maguuson, PROC. NATL. ACAD. SCI. U.S.A. 83:3228 (1986). When n=2 and one mismatch is allowed, four of these sequences are found. There is an overlap in three of these between the sequence defined by Caput et al. and that defined by Reeves et al.

Figure 11:
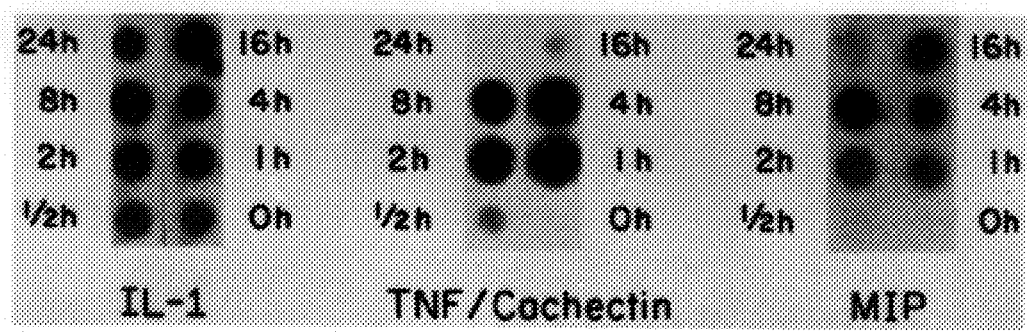
FIG. 11 is an autoradiogram of a northern blot of total RNA from RAW 264.7 cells, a transformed murine macrophage cell line. The cells were stimulated with LPS at 2 μg/ml in serum-free medium for 6 hours. Control cells were given serum-free medium with no added LPS for 6 hours. The total amount of RNA loaded in each lane is indicated on the figure.
Figure 12:
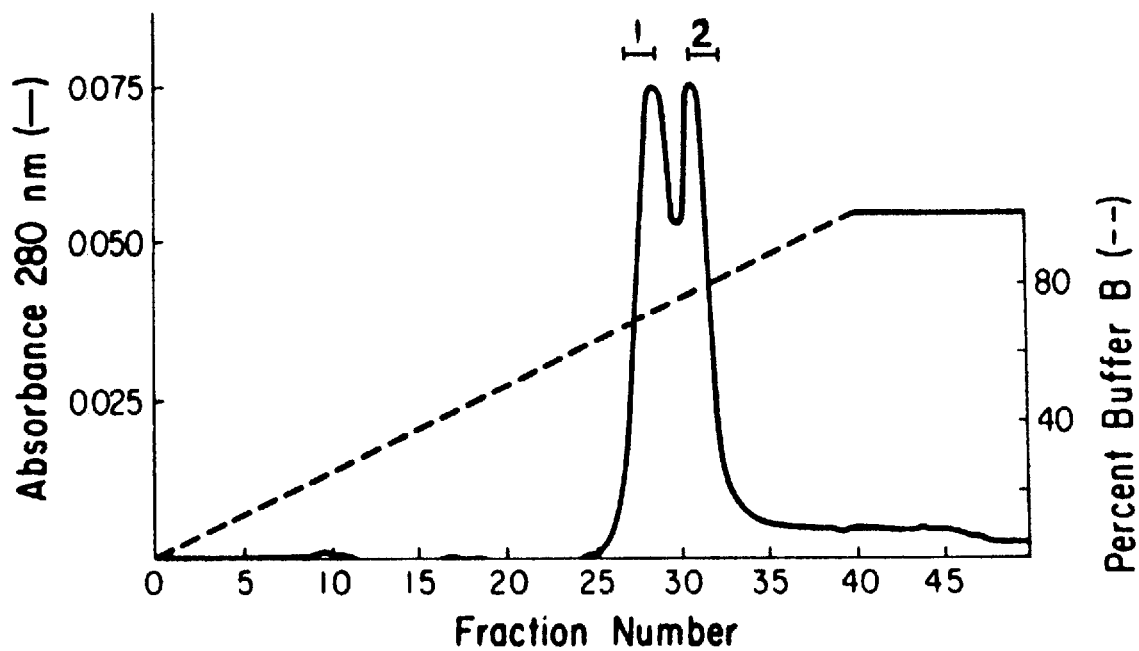
FIG. 12 is a depiction of a time-course study of RAW 264.7 mRNA induction by LPS. The time course is measured in hours. All three probes were plasmid cDNA clones labeled with α-[$^{32}$P] dCTP.

Since MIP-1 is an inducible protein, the expression of murine MIP-1α mRNA by Northern blot hybridization in RAW 264.7 cellular DNA was also studied. As shown in FIG. 11, total RNA from LPS-induced cells exhibited a positive hybridization band with an estimated size of 800 bp, while total RNA from uninduced cells showed very little of a positive signal at that or any other size. In a time-course study of the induction of murine MIP-1α mRNA by endotoxin in these same cells (FIG. 12), murine MIP-1 mRNA is detected within 1 hour after LPS stimulation and peaks between 8–16 hours after LPS stimulation. This time course differs from the appearance of either murine TNF-α/cachectin or IL-1α mRNAs when their respective plasmid probes were hybridized to the same blot.

An mRNA produced by human tonsillar lymphocytes in response to mitogen was reported by Obaru, M. Fukuda, S. Maeda, and K. Shimada, J. BIOCHEM, 99:885 (1986). While the sequence is not listed in the Dayhoff protein data base or the GenBank genetic sequence data base, there is a 75.3% amino acid sequence similarity between that protein and murine MIP-1α. The relationship between these proteins is not known.

Results of N-terminal sequence analysis of the higher molecular weight component of MIP-1 (now referred to as MIP-1β) is shown in FIG. 14B. The "minor" residues observed at positions 3 and 7 in the original N-terminal amino acid sequence correspond to amino acid differences between MIP-1β and MIP-1α. In FIG. 14C the original N-terminal amino acid consensus sequence for native MIP-1 is given for comparison.

A cDNA clone containing the coding sequence for MIP-1β was isolated and characterized. To accomplish this, a cDNA library from LPS-stimulated RAW 264.7 cells was prepared. The oligonucleotide probe pool used to screen the cDNA library was generated against the sequence underlined in FIG. 14B. Three of these seven MIP-1β amino acids differ from the corresponding sequence of MIP-1α. The probe pool utilized for screening the library was

The third position choices were made based on the codon usage reported for cloned murine genes (F. Sanger, S. Nicklen, and R. Coulson, PROC. NATL. ACAD. SCI. (U.S.A.) 74:5463, (1977) and the codon usage of MIP-1α.

Utilizing the labeled probe pool, the library was screened under conditions of moderate stringency. Two independent clones were isolated out of 4×10$^5$ recombinant phage plaques screened. This was a considerably lower frequency than expected. Upon DNA sequencing of the isolated clones, it was found that the choice of C for the third position of the Ser5 codon was incorrect. The correct choice was actually a T thereby resulting in no perfect match of any of the probe pool sequences to the actual MIP-1β sequence. Thus, MIP-1β sequence representation in the library is likely to be underestimated based on hybridization with the above probe pool. Subsequent screening of the library with unique oligonucleotide probes specific for comparable regions of MIP-1α and MIP-1β indicate that MIP-1β-specific sequences are 5-fold less abundant than MIP-1α sequences.

Following plaque purification, insert DNA (≈700 bp) from the two positive recombinant phage was shown to cross-hybridize to the MIP-1α cDNA probe. Insert cDNA was isolated from each recombinant phage population and cloned into m13 from which the complete nucleotide sequence was determined. The two nucleotide sequences differed only in the length of 5' untranslated sequence present. The longer nucleotide sequence is presented in FIG. 15.

The MIP-1β cDNA is 650 base pairs (which by primer extension analysis is no more than 11–12 nucleotides short of a complete cDNA sequence). The nucleotide sequence of MIP-1β contains a single open reading frame beginning with the first ATG codon encountered at the 5' end of the sequence (nucleotides +62 to +64) after an in-frame stop codon. The methionine specified by this codon defines the start of a putative signal sequence (residues −23 and −1) with characteristic features including an α-helix and a centrally located hydrophobic region (D. Perlman, and H. O. Halvorson, J. MOL. BIOL., 167:391 (1983)). The sequence surrounding this ATG codon conforms to the consensus sequence shared by many mRNAs of higher eukaryotes (M. Kozak, NATURE, LONDON, 308:241 (1984)).

The TGA termination triplet is located 91 codons downstream of the initiating codon. The 3' untranslated region of MIP-1β is comprised of 315 nucleotides and contains the hexanucleotide AATAAA (nucleotides +283 to +288) which precedes the site of polyadenylation in many eukaryotic mRNAs (N. J. Proudfoot and G. G. Brownlee, NATURE, LONDON 263:211 (1976)).

There is a single sequence at nucleotides +174 to +181 which precisely matches a known cytokine 3' untranslated consensus sequence (TTATTTAT) that is characteristic of many immunomodulatory proteins. In addition, there are two additional sequences present that have a single mismatch to this consensus sequence (nucleotides +165 to +175 and nucleotides +185 to +192.

The mature protein sequence, starting at position 1, is 69 amino acids in length. The molecular weight of the mature protein as determined from its cDNA clone is 7832 daltons which agrees with the molecular weight prediceted by SDS-PAGE. The amino acid sequence predicted from the cloned DNA sequence is consistent with the first 13 amino acids obtained from N-terminal amino acid sequencing of purified native MIP-1β.

MIP-1β has a single N-linked glycosylation site present in the mature protein at amino acids 53 to 55 (Asn-Pro-Ser). Whether native MIP-1 is actually glycosylated at this position has not yet been determined, but it is well recognized that proline at position X in the consensus Asn-X-Ser,Thr signal for N-linked glycosylation results in impaired or no glycosylation at that site (I. Moronen, and E. Karajalainen, BIOCHEM. BIOPHYS. ACTA., 788:364 (1984)).

Figure 16:
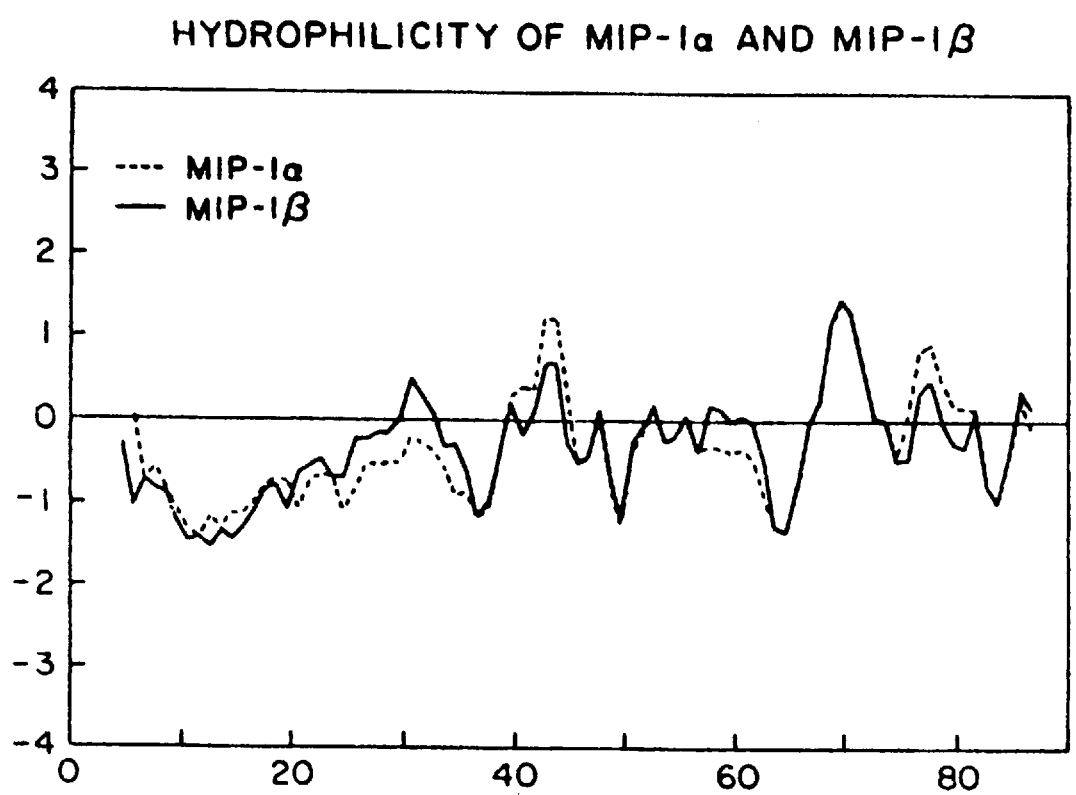
FIG. 16 is a graphical depiction of estimated local hydropathicity along the length of MIP-1α (- - -) and MIP-1β (—) calculated by an adaptation of the algorithm of Hopp and Woods.

Hydropathicity plots for MIP-1α and MIP-1β which estimate the predicted polarity profiles of the two proteins are shown in FIG. 16. It is clear from FIG. 16 that the local polarity distributions within MIP-1α and MIP-1β are strikingly similar.

The entire nucleotide sequence of the murine MIP-1β cDNA was compared to sequences in the Genbank nucleotide database (rodent, primate, other mammals and other vertebrate libraries) as well as to the MIP-1α cDNA sequence (G. Davatelis, S. D. Wolpe, C. Luedke, P. Tekamp-Olson, J. Merryweather, K. Hermsen, C. Gallegos, D. Coit, and A. Cerami, J. EXP. MED., 167:570 (1988)). MIP-1β and MIP-1α cDNAs are 56.7% identical. The only significant homology found in Genbank was the human LD78 cDNA clone isolated from a T cell lymphocyte cDNA library on the basis that its mRNA was induced by either the tumor promoter PMA or by phytohemagglutinin (K. Obaru, M. Fukada, S. Maeda, and K. Shimada, J. BIOCHEM., 99:885 (1986)). Murine MIP-1β cDNA showed 57.1% identity in a 592 nucleotide overlap to human LD78 cDNA, murine MIP-1α cDNA showed even higher homology, 69% identity in a 746 nucleotide overlap.

When the predicted amino acid sequence of MIP-1β was tested for homology to sequences in the Dayhoff data base using the p-Fast-D computer homology algorithm, no strikingly high homology was found. However, comparison of the predicted protein sequences of murine MIP-1β, murine MIP-1α, human LD78 as well as the recently reported predicted sequences for the PDGF, IL-1, a murine cytokine (JE) inducible by double-stranded RNA (P. R. Burd, G. J. Freeman, S. D. Wilson, M. Berman, R. DeKruyff, P. R. Billings, and M. E. Dorf, J. IMMUNOL., 139:3126 (1987) and a murine T-cell activation protein (TCA3) (B. F. Rollins, E. D. Morrison, and C. D. Stiles, PROC. NATL. ACAD. SCI. U.S.A., 85:3738 (1988)) indicates that these proteins are noticeably homologous. The deduced amino acid sequence of MIP-1β shows 59.8% identify to that of MIP-1α and 58.7%, 38.9% and 21.9% identity to the predicted amino acid sequences of LD78, JE and TCA3 respectively. Common to all these sequences is the presence of four conserved cysteines in each of the mature peptide sequences. Interestingly, the predicted amino acid sequence of murine MIP-1α is more homologous to that of human LD78 (75.3% identify) than it is to the predicted amino acid sequence of murine MIP-1β (59.8% identity). Thus, these proteins share similarities in sequence that appear to define a family of peptides which may be involved in inflammatory and/or immune responses.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method of treating inflammation and/or fever in mammals, comprising administering to a mammal an inflammation- and/or fever reducing amount of a specific binding partner of an inflammatory cytokine, wherein said inflammatory cytokine is a protein that is capable of binding to heparin, inducing localized inflammation characterized by polymorphonuclear cell infiltration when administered subcutaneously and inducing in vitro polymorphonuclear cell chemokinesis, while lacking the ability to suppress the activity of the anabolic enzyme lipoprotein lipase, cause the cytotoxicity of cachectin/TNF-sensitive cells, stimulate the blastogenesis of endotoxin-resistant C3H/HeJ thymocytes, or induce the production of cachectin/TNF by primary thioglycollate-elicited mouse macrophage cells, which protein is anionic under physiological conditions and has an apparent molecular weight of approximately 8000 daltons as determined by SDS-PAGE.

2. The method of claim 1 wherein said inflammatory cytokine tends to form aggregates of high molecular weight greater than about $10^6$ daltons in low salt buffers.

3. The method of claim 1 wherein said cytokine is capable of inducing fever in rabbits and inducing superoxide formation or respiratory burst in human neutrophils in vitro.

4. The method of claim 1 wherein said inflammatory cytokine is derivable from animal cells incubated with a stimulator material.

5. The method of claim 1 wherein said inflammatory cytokine is derived from cells which are produced by clonal replication.

6. A method for preventing the occurrence of inflammation and/or fever in mammals comprising administering a specific binding partner of an inflammatory cytokine in an amount effective to avert the onset of said inflammation and/or said fever, wherein said inflammatory cytokine is a protein that is capable of binding to heparin, inducing localized inflammation characterized by polymorphonuclear cell infiltration when administered subcutaneously and inducing in vitro polymorphonuclear cell chemokinesis, while lacking the ability to suppress the activity of the anabolic enzyme liprotein lipase, cause the cytotoxicity of cachectin/TNF-sensitive cells, stimulate the blastogenesis of endotoxin-resistant C3H/HeJ thymocytes, or induce the production of cachectin/TNF by primary thioglycollate-elicited mouse macrophage cells, which protein is anionic under physiological conditions and has an apparent molecular weight of approximately 8000 daltons as determined by SDS-PAGE.

7. The method of claim 6 wherein said inflammatory cytokine tends to form aggregates of high molecular weight greater than about $10^6$ daltons in low salt buffers.

8. The method of claim 6 wherein said inflammatory cytokine is capable of inducing fever in rabbits and inducing superoxide formation of respiratory burst in human neutrophils in vitro.

9. The method of claim 6 wherein said inflammatory cytokine is derived from cells which are produced by clonal replication.

10. The method of claim 6 wherein said inflammatory cytokine is derivable from animal macrophage cells incubated with a stimulator material.

11. The method of claim 1 wherein the inflammatory cytokine has the amino acid sequence as set forth in FIG. 10.

12. The method of claim 1 wherein the inflammatory cytokine is a peptide doublet having the amino acid sequences as set forth in FIGS. 10 and 15.

13. The method of claim 1 wherein the specific binding partner of the inflammatory cytokine is an antibody.

14. The method of claim 6 wherein the inflammatory cytokine has the amino acid sequence as set forth in FIG. 10.

15. The method of claim 6 wherein the inflammatory cytokine is a peptide doublet having the amino acid sequences as set forth in FIGS. 10 and 15.

16. The method of claim 6 wherein the specific binding partner of the inflammatory cytokine is an antibody.

* * * * *